US012758212B2

(12) United States Patent
Ouyang et al.

(10) Patent No.: US 12,758,212 B2
(45) Date of Patent: Oct. 13, 2026

(54) TENDON SUTURE INSTRUMENT

(71) Applicant: Liangzhu Laboratory, Hangzhou city (CN)

(72) Inventors: Hongwei Ouyang, Haining City (CN); Jie Zhang, Haining City (CN); Yi Hong, Haining City (CN)

(73) Assignee: Liangzhu Laboratory, Hangzhou City (CN)

( * ) Notice: Subject to any disclaimer, the term of this patent is extended or adjusted under 35 U.S.C. 154(b) by 130 days.

(21) Appl. No.: 18/667,546

(22) Filed: May 17, 2024

(65) Prior Publication Data

US 2024/0423609 A1 Dec. 26, 2024

(30) Foreign Application Priority Data

Jun. 25, 2023 (CN) ......................... 202310755061.8

(51) Int. Cl.
*A61B 17/04* (2006.01)
*A61F 2/08* (2006.01)

(52) U.S. Cl.
CPC ........ *A61B 17/0482* (2013.01); *A61F 2/0811* (2013.01)

(58) Field of Classification Search
CPC ............ A61B 17/0482; A61B 17/0401; A61B 2017/0464; A61F 2/0811
See application file for complete search history.

(56) References Cited

U.S. PATENT DOCUMENTS

| | | | | |
|---|---|---|---|---|
| 6,200,327 B1 * | 3/2001 | Assal | ................. | A61B 17/0469 606/148 |
| 6,322,571 B1 * | 11/2001 | Adams | ............... | A61B 17/0482 606/151 |
| 2015/0245841 A1 * | 9/2015 | Linder | ................. | A61B 17/068 606/151 |
| 2024/0350143 A1 * | 10/2024 | Yee | .................. | A61B 17/07207 |

* cited by examiner

*Primary Examiner* — Phong Son H Dang
(74) *Attorney, Agent, or Firm* — Muncy, Geissler, Olds & Lowe, P.C.

(57) ABSTRACT

Disclosed is a tendon suture instrument, including a chamber. One end of the chamber is provided with an opening, and the chamber is used for accommodating a sutured tendon tissue. The tendon tissue can enter the chamber through the opening of the chamber when needing to be sutured. The chamber is defined by a wall, and a first wiring channel and a first needle guide hole are arranged on the wall.

20 Claims, 25 Drawing Sheets

Schematic diagram of arrangement of wiring channels and needle guide holes on right wall Schematic diagram of wiring channels and needle guide holes on left wall from the same perspective as the right wall Schematic diagram of arrangement of wiring channels and needle guide holes on top surface Schematic diagram of arrangement of wiring channels and needle guide holes on bottom surface from the same perspective Schematic diagram of arrangement of wire guiding channels and needle guide holes on right wall Schematic diagram of wire guiding channels and needle guide holes on left wall from the same perspective

TENDON SUTURE INSTRUMENT

CROSS-REFERENCE TO RELATED APPLICATIONS

This application claims priority to the Chinese Patent Applications; Application No.: 2023107550618, filed on Jun. 25, 2023; all of which are part of the present invention.

BACKGROUND OF THE INVENTION

Field of the Invention

The present invention belongs to surgical instruments for suture, and particularly, relates to a tendon suture instrument and a use method therefor.

Description of the Related Art

Tendons are important fibrous connective tissues that connect muscles and bones, playing a crucial mechanical regulatory role in the human motion system to maintain joint load circulation and protect surrounding tissues. Common tendon injuries in clinical practice include rotator cuff injury, rupture of patellar tendon, achilles tendinitis, acute rupture of achilles tendon, etc. Tendon rupture causes local severe pain, often leading to the loss of exercise ability of patients and immense physical and mental pressure on patients. It is also one of the main causes of cessation of sports careers of professional track and field athletes.

So far, there is still significant controversy in clinical practice regarding the best therapeutic method for tendon rupture. Currently, there are two main approaches, namely conservative treatment and surgical treatment. Although the conservative treatment can avoid surgical complications such as wound infection and nerve injury, incomplete healing of conservative treatment increases the risk of re-rupture. Therefore, tendon rupture tends to early surgical treatment. For the methods for the surgical treatment of tendon rupture, double cross suture, Kessler suture, figure of eight suture, and other minimally invasive suture methods are commonly used. However, the mechanical strength of suture of these methods is relatively poor, and the suture effect depends to a certain extent on the operator's operational experience. When the same suture method is used by different operators, the final suture effects and the postoperative functional recovery degrees of patients often vary greatly (for experienced operators having good suture skill, the suture effect is good, suture mechanics is stable, the postoperative plaster assisted fixation time is short, and the incidence of complications of tendon adhesion of patients is low, while for inexperienced young operators, the effects are opposite).

In existing technologies, there are also techniques that rely on surgical instruments as auxiliary tools to suture tendons, for example, Patent number: 202010127942.1, Patent name: Tendon Suture Apparatus and Use Method Therefor; the apparatus mainly functions by means of the interaction of a tendon clamp, needle guide holes, and a locking structure to achieve cross braided suturing of ruptured tendons and achieve the purpose of anastomosis of ruptured tendon ends. However, due to the large volume of the tendon clamp itself, it is not suitable for small-space ruptured tendon ends, for example, the tendon suture apparatus is not suitable for rupture of knee anterior cruciate ligament or rupture of achilles tendon; secondly, the design of the needle guide holes can only complete one suture method, limiting the selection of suture methods for different parts.

BRIEF SUMMARY OF THE INVENTION

In order to overcome the shortcomings of existing traditional techniques, the present invention provides a tendon suture instrument capable of standardized operation and a use method therefor. The suture instrument is not only suitable for the needs of different muscle suture scenarios, but also more flexible and convenient to operate.

Therefore, in one aspect, the present invention provides a suture instrument, which is a device or apparatus for tendon suture. In some implementations, the suture instrument includes a chamber having an opening, the chamber includes a wall defining the chamber, and the wall is provided with wiring channels, wherein needle guide holes are arranged on the wiring channels, or the wall includes needle guide holes, so that a suture needle relies on the needle guide holes to allow a suture wire to pass through a tendon tissue. In some implementations, the chamber is arranged for accommodating tendons. In some implementations, the tendons enter the chamber through an inlet and are located inside the chamber, and the tendons are provided with suture wires.

These wiring channels cooperate with the needle guide holes to allow the tendons that need to be sutured to be provided with the suture wires, thereby suturing the ruptured tendons. In some implementations, each of the ruptured tendons (there are usually two ruptured tendons) is provided with a suture wire, so that the rupture position of the two tendons is in a closed state by means of the connection of the suture wires. This achieves muscles to be produced and connected together in later stages.

In some implementations, the suture instrument further includes a gripping element for gripping a tendon, and the gripping element is used for allowing the tendon to enter the chamber. In some implementations, the grabbing element allows the tendon to enter the chamber through the opening of the chamber. In some implementations, the gripping element can also allow the tendon to be in a relatively fixed position inside the chamber, making suture convenient. In some implementations, the gripping element can also release the gripped tendon, allowing the tendon to leave the chamber. In some implementations, some gripping elements can move in the chamber, and by means of the path of movement, the gripping elements can connect the tendons, allowing the tendons connected by the gripping elements to enter the chamber, and fixing the tendons in the chamber, or allowing the tendons to leave the chamber. After or in the process that the latter tendon leaves the chamber, the gripping element is separated from the tendon.

In some implementations, the gripping element has a function similar to a fixture, a plier, or a clamp. During the movement in the chamber, the clamp is in an opened or closed state. When in the opened state, the clamp is used for connection to the tendon. When in the closed state, the tendon is in a connected state with the clamp, making it convenient for the gripping element to drag the tendon to enter the chamber. When the clamp is in the opened state or during the process from closing to opening, the tendon is detached from the gripping element. Hence, in some implementations, when the gripping element is in a first position in the chamber, the tendon is gripped by the gripping element or the gripping element is not used for gripping the tendon; when the gripping element is in a second position in the chamber, the tendon enters the chamber through the opening of the chamber and is fixed in the chamber; when or in the process that the gripping element returns from the second position to the first position in the chamber, the gripping element allows the tendon to leave the chamber.

In some implementations, some gripping elements are located in the chamber. In an initial position, when needing to be used for gripping the tendons, the gripping elements extend from a section of the opening of the chamber, and the clamp is opened at this time. When the gripping elements move towards the interior of the chamber, the clamp is closed to clamp or grip the tendons, and at the same time, drag the tendons into the chamber, and at this time, the clamp is still closed. After suture is completed, the gripping elements are allowed to extend out of the opening of the chamber from the interior of the chamber. At this time, the clamp on the gripping elements is opened, thereby releasing the tendons from the chamber.

In some implementations, the closure or closing of the clamp on the gripping element is automatic. In some implementations, the clamp has two upper and lower elastic clamping pieces. The clamping pieces extend out of the chamber and are automatically opened due to the elasticity of the clamping pieces, and at this time, the tendon is located between the clamping pieces. When the clamping pieces retract into the chamber, the opened clamping pieces are closed, so that the tendon is in a fixed connection with the clamp, allowing the clamp to drive the tendon to enter the chamber to be in a relatively fixed position. After the tendon suture is completed, the clamp extends out of the chamber again and is automatically opened to release the tendon. In this way, the suture of one of the ruptured tendons is completed, allowing the suture wire to be arranged on the tendon. In the same way, using the similar operation, the other one of the ruptured tendons is also provided with a suture wire, so that the suture wires on the two tendons are connected, allowing the ruptured ends of the tendons to come into contact.

In some implementations, a sleeve is further arranged on the gripping element. The sleeve moves relative to the gripping element, so that the clamp on the gripping element is in the opened or closed state, allowing the gripping element to be in a connected or unconnected state to the tendon. In some implementations, the gripping element has a fixed position in the chamber, so that the tendon also has a fixed position in the chamber, making suture after fixation convenient.

In some implementations, it is a preferred implementation that the gripping element is provided with the clamp, the gripping element may also be provided with a similar hook, a hooked needle, or any others means. Any state where the structure on the gripping element is connected or unconnected to the tendon is automatic, alternatively, the connection is automatic, while the unconnection of the gripping element to the tendon needs manual separation. These specific implementations can all be specific implementations of the present invention without violating the essence of the present invention.

The term "suture" in the present invention only means "suturing" in some cases, allowing the tendon to be provided with a suture wire (such as a medical suture wire). For example, for a ruptured tendon, usually, a complete tendon is ruptured into two pieces, with each piece provided with a suture wire. This meaning can also be referred to as suture. When both the two pieces are provided with the suture wires, the two pieces contact each other at the ruptured position by means of the suture wires, which means "suture". In fact, it means to pull the suture wires on the tendons to make the ruptured tendons contact each other at the ruptured position.

In some implementations, the chamber is provided with wiring channels and needle threading holes or needle guide holes, or needle guide channels, allowing the tendons located in the chamber to be provided with the suture wires by relying on the movement of a suture needle in the needle threading holes. Due to different suture methods or different directions of movement of the suture needle in the needle holes, the formation or structure of the arrangement of the suture wires on the tendons is different.

In some implementations, these wiring channels and needle threading holes are arranged on a wall of the chamber. The needle threading holes or the needle guide holes here may be channels, which generally have an inlet or an outlet at both ends. The inlet and the outlet are channels through which the needle threads, and these channels have different lengths. In some implementations, the thickness of the channels is equal to that of the wall of the chamber, or the needle guide channel is the thickness of the wall of the chamber. Hence, the needle threading holes or the needle guide holes, or the needle guide channels here refer to holes or channels that guide the suture needle, allowing the suture needle to arrange in different ways or different paths the suture wires on a tendon tissue that needs to be sutured. So, the meanings of "needle threading holes"; "needle guide holes"; "needle threading channels"; or "needle guide channels" can be interchanged, representing the terminology having the same structure or the same function.

In some implementations, the wiring channels are provided with needle threading holes. In such implementations, these wiring channels are usually in the form of ditches or grooves provided on the wall of the chamber, but these ditches or grooves penetrate through the wall of the chamber, similar to forming multiple hollow structures on the wall of the chamber, and the hollow parts shown the form of channels. Hence, the arrangement of the channels here allows the suture wire to be distributed in a ditch or groove on the surface of the tendon. When the tendon is located in the chamber, the needle moves in the needle threading holes, the suture needle includes a needle head and a needle tail, the needle tail is provided with a suture wire, and the needle head threads through the tendon for the process of wire threading by means of the needle guide holes. In this way, the suture wire is arranged on the surface of the tendon by means of the wiring channels. Hence, when the suture needle with the suture wire moves in different movements ways through the needle guide holes on the channels, different forms of wiring ways are set up on the tendon. It can be understood here that the needle threading holes are arranged at the two ends or in the middle of the channels, and the holes become part of the channels.

In some implementations, such wiring channel having the needle threading holes can be arranged on the wall of the chamber, and may be multiple. These multiple wiring channels may be distributed on two sides of the chamber, or distributed on two sides of the chamber, respectively. For example, wiring channels are arranged on the right side of the chamber, and wiring channels are also arranged on the opposite side of the chamber. Of course, two sets of wiring channels may also be symmetrically distributed along the central axis of the chamber. In this way, such distribution way generally allows the suture needle to rely on the needle threading holes on the wiring channels to pass through the tendon for suture, so that the suture wire passes through the cross section of the tendon. Alternatively, when being guided using the needle guide holes, the suture needle enters from the needle threading hole on the right side and exits from the needle guide hole of the wiring channel on the opposite side, or the suture needle exits from the needle threading hole on the right side and enters from the needle guide hole of the wiring channel on the opposite side. The penetrating through the cross section of the chamber or the cross section of the tendon here refers to that the needle needs to pass through the wiring channel arranged on the opposite side. Relative to the longitudinal direction of the chamber, the needle reciprocates left and right to drive the suture wire to reciprocate, each movement basically passes through the entire cross section of the chamber, and when the tendon is contained in the chamber, the movement basically passes through the cross section of the tendon tissue. Forming similar “cross weaving” is the suture wire passing through the tendon tissue, generally passing through the entire cross section of the tendon from one side of the tendon. The cross weaving methods include a Bunnel method and an improved Bunnel method. A common feature of these different forms of weaving methods is that the suture wire passes through the cross section of the tendon, which can also be understood that the suture wire passes through the cross section of the chamber under the action of the suture needle, or passes from the needle guide hole of the wiring channel on one side to the needle guide hole of the wiring channel on the other side, or reciprocates multiple times in the opposite direction. The “cross section” here refers to the section after cross cut of the chamber, on which the suture needle enters from the needle hole on one side of the chamber and exits from the needle hole on the other side of the chamber under the guidance of the needle guide holes, and the needle holes are distributed on two sides of the chamber, which is the different meaning and way from the subsequent distribution of needle holes on one side of the chamber.

The following will elaborate in different ways. The two sides of the chamber here generally refer to being distributed on different surfaces of the chamber. For example, if the cross section of the chamber is circular or roughly circular, the chamber has a diameter, and the wiring channels are distributed on the corresponding curved surfaces on the left and right sides of the diameter. Of course, the chamber as a whole is either a cube or a cuboid, and the wiring channels may be arranged on two opposite surfaces. Of course, in some implementations, the wiring channels are symmetrically arranged on the wall of the chamber along the longitudinal axis of the chamber, or are mirrored to each other.

In some implementations, the wiring channels are symmetrically arranged on the wall of the opening of the chamber and symmetrical needle guide holes are arranged on the wiring channels, allowing the suture needle to pass through the needle guide holes to pass through the cross section of the chamber. If the tendon is contained in the chamber, the suture wire passes through the cross section of the tendon.

In some implementations, a first wiring channel and a second wiring channel are arranged on the wall of the chamber, a first needle guide hole and a second needle guide hole are arranged at two ends of the first wiring channel, and a third needle guide hole and a fourth needle guide hole are arranged at two ends of the second wiring channel; a third wiring channel and a fourth wiring channel axisymmetrical to the first wiring channel and the second wiring channel along the chamber are arranged on the wall of the chamber, respectively, and a fifth needle guide hole and a sixth needle guide hole are arranged at two ends of the third wiring channel; and a seventh needle guide hole and an eighth needle guide hole are arranged at two ends of the fourth wiring channel. When passing into the first needle guide hole of the first wiring channel, a first suture needle can pass out of the third needle guide hole of the second wiring channel, further, the first suture needle first passes into the second needle guide hole of the first wiring channel and passes out of the seventh needle guide hole of the fourth wiring channel, and then the first suture needle passes into the eighth needle guide hole of the fourth wiring channel and passes out of the needle guide hole on the other side wall; a second suture needle first pass into the fourth needle guide hole of the second wiring channel and passes out of the sixth needle guide hole of the third wiring channel, and then the second suture needle passes into the fifth needle guide hole of the third wiring channel and passes out of the needle guide hole on the other side wall. So, the suture wire between the first suture needle and the second suture needle is arranged on the surface of the tendon along the first wiring channel. The first wiring channel and the third wiring channel are arranged at the position near the opening of the chamber that serves as an initial suture position of the suture needle, and the position far away from the opening of the chamber serves as the end of the suture (cross weaving).

In some implementations, a first wiring channel is arranged on a side wall of the chamber along a longitudinal direction of the chamber, and a second wiring channel is arranged symmetrical to the first wiring channel along a longitudinal axis of the chamber. A first needle guide hole, a second needle guide hole and a third needle guide hole are arranged sequentially on the first wiring channel, and a fourth needle guide hole, a fifth needle guide hole and a sixth needle guide hole are arranged sequentially on the second wiring channel, wherein the first needle guide hole and the fourth needle guide hole are arranged in a symmetrical communication manner, the second needle guide hole and the sixth needle guide hole are arranged in a communication manner, and the third needle guide hole and the fifth needle guide hole are arranged in a communication manner. In this way, when a first suture needle and a second suture needle connected to a suture wire are used for tendon suture, the first suture needle enters from the first needle guide hole of the first wiring channel and exits from the fourth needle guide hole of the second wiring channel, so that the first suture needle is located on one side of the second wiring channel, and the second suture needle is distributed on one side of the first wiring channel. Further, the first suture needle enters from the fifth needle guide hole and exits from the third needle guide hole, and the second suture needle enters from the second needle guide hole and exits from the sixth needle guide hole. In this way, the suture wire is arranged on a tendon in a cross manner (if the tendon is in the chamber), and the surface of the tendon shows a running wiring way. The first needle guide hole of the first wiring channel and the third needle guide hole of the second wiring channel are close to an inlet of the chamber, or the first needle guide hole, the second needle guide hole and the third needle guide hole are arranged in sequence from near to far to near along the longitudinal direction of the chamber near the inlet of the chamber, and on the second wiring channel, the third needle guide hole, the fourth needle guide hole, and the fifth needle guide hole are also arranged in sequence. In some implementations, the size of the needle guide hole is essentially equal to the size of the wiring channel, or the width of the wiring channel is little different from the width of the needle guide hole (Bunnel weaving method).

In some implementations, a first wiring channel and a second wiring channel are arranged on the wall of the chamber, and a third wiring channel and a fourth wiring channel are arranged symmetrical to the first wiring channel and the second wiring channel on the wall of the chamber, wherein the first wiring channel is not in communication with the second wiring channel, and the third wiring channel is not in communication with the fourth wiring channel. In some implementations, a length of the first wiring channel is less than that of the second wiring channel. In some implementations, a length of the third wiring channel is greater than that of the fourth wiring channel. In some implementations, a projection of the first wiring channel is located in or on the third wiring channel, or the length of the first wiring channel is less than that of the third wiring channel. In some implementations, a length of the fourth wiring channel is less than that of the second wiring channel. In some implementations, one or more needle threading holes are arranged on the first wiring channel, the second wiring channel, the third wiring channel, and the fourth wiring channel. In some implementations, the first wiring channel, the second wiring channel, the third wiring channel, and the fourth wiring channel are arranged along a longitudinal direction of the chamber. In some implementations, the size of the needle guide hole is essentially equal to the size of the wiring channel, or the width of the wiring channel is little different from the width of the needle guide hole (improved Bunnel weaving method).

Of course, these wiring channels having needle guide holes may also be asymmetrically distributed. At this time, the suture needle is only guided by the needle threading holes to arrange the suture wire on one side of the tendon. Such method does not pass through the entire cross section of the tendon and can be called a running weaving method. A running locking weaving method is derived under the running weaving method. When a double-needle method is used, the arrangement of the suture wire on the tendon can be completed by means of the different movement ways of two suture needles in the needle threading holes. In some implementations, the wiring channels are arranged on the wall of the chamber, and are also provided with needle guide holes. However, under the action of the needle guide holes, the suture needle does not penetrate through the center position of the chamber or does not penetrate through the cross section of the chamber, but only penetrates through part of the chamber, to arrange the suture wire on the tendon. It can be understood that on the trajectory route of movement of the suture needle guided by such needle guide holes, the suture needle always moves between the wiring channels on the same side, rather than moving on the opposite side of the chamber. This is different from the cross weaving method mentioned earlier. When a double-needle wiring method is used, the suture wires are separately arranged on the tendon, respectively. Similarly, on the tendon, the suture wires do not penetrate through the entire cross section of the tendon, but rather penetrate through part of the tendon.

In some implementations, the wiring channels are arranged on one side of the wall of the chamber, and are provided with needle guide holes. In some implementations, a first wiring channel and a second wiring channel are arranged on the same side of the wall of the chamber, and one or more needle guide holes are arranged on each wiring channel. For example, two ends of the first wiring channel are each provided with one needle guide hole, and two ends of the second wiring channel are each provided with one needle guide hole. When the needle guide holes are used to guide a suture needle to move, the suture needle enters from the needle guide hole at one end of the first wiring channel and exits from the needle guide hole of the second wiring channel. For convenience, the first wiring channel may be close to the second wiring channel, or the first wiring channel is arranged parallel to the second wiring channel, and a needle always passes between the first wiring channel and the second wiring channel. Here, the first wiring channel and the second wiring channel are arranged on the same side wall of the chamber, so the suture needle moves up and down on the wall of one side of the chamber. Hence, in some implementations, a first wiring channel and a second wiring channel are arranged on one side of the wall of the chamber, and a first needle guide hole (e.g., an upper position) and a second needle guide hole (a lower position) are arranged on the first wiring channel. For example, at two ends of the channel, a third needle guide hole (also an upper position) and a fourth needle guide hole (a lower position) are arranged on the second wiring channel. When suture is performed, the suture needle enters from the second needle guide hole of the first wiring channel and then exits from the third needle guide hole of the second wiring channel. When suture is performed again, the suture needle enters from the fourth needle guide hole of the second wiring channel and exits from the fifth needle guide hole (upper) of the third wiring channel, so that a suture wire is arranged on a surface of a tendon through the wiring channels if the tendon is located in the chamber. It can be understood that in this way, multiple wiring channels can be arranged on one side, and during each suture, the suture needle can enter from the first channel and exit from the adjacent second channel, and then enter from the same channel and exit from another channel (running weaving method).

In some implementations, in order to simultaneous or synchronous suture using double needles, channels can also be arranged on the other side of the chamber referring to the above way. In this way, at the beginning of the initial process, the suture needles need to pass through the chamber from the needle guide hole of one side of the wiring channel and come out from the wiring channel on the other side, and then separately move on the wiring channel of respective side, rather than passing through the center position of the chamber or penetrating though the cross section of the chamber. Double-needle suture is only a preferred implementation for convenient operation, and of course, it does not rule out the use of single-needle suture on one side.

In some implementations, sometimes in order to more fix the suture wire on the tendon, the latter is for being firmer. A wiring channel is arranged on one side of the chamber, and the wiring channel is a whole region, or a missing region is on the wall of the chamber, and one or more needle guide holes are arranged on the region. In some implementations, the needle guide holes are arranged on two sides of the wiring region. The "wiring region" here generally refers to arranging at least two or more needle guide holes on one side of the region, and the wiring channel is generally provided with one needle threading hole at one end of the channel. The wiring region here may be roughly a rectangle, a square, or any other shape. Unlike the wiring channel, on the region, any side is provided with a plurality of needle guide holes, and the region is all missing regions of the side wall of the chamber. In some implementations, the wiring region is located on one side of the chamber, one or two or more needle guide holes are arranged on one side of the wiring region along a longitudinal direction of the chamber, and one or two or more needle guide holes are correspondingly arranged on the other side or edge of the wiring region. In some implementations, when the suture needle enters the chamber along the needle guide holes, when the suture needle passes out of the needle guide hole on one side of the wiring region, a suture wire is allowed to surround a needle head one round, and then the needle head is allowed to pass through a region formed by the suture wire. When next needle threading, still when the suture needle passes out of the adjacent needle guide hole on one side, the suture wire is allowed to surround the needle head one round, and then the needle head is allowed to pass through a region formed by the suture wire. In this way, on the side where the needle head comes out, the suture wire is arranged on the tendon that needs to be sutured, and a knot is formed at the place where a tip of each suture needle is exposed, and each knot is connected by the suture wire. In some implementations, the suture wire surrounds the needle head in a clockwise or counterclockwise direction.

In some implementations, at least two or more needle guide holes (first and second needle guide holes) are arranged on one side of the wiring region, and the needle guide holes are arranged to allow the needle head of the suture needle to come out. At least two or more needle guide holes (third and fourth needle guide holes) are arranged on the opposite side of the wiring region, and the needle guide holes are for the needle head to enter. When suture is performed using the suture needle, the suture needle enters from the third needle guide hole and exits from the first needle guide hole, when the needle tip comes out, the suture wire passes clockwise in front of the needle tip, and then the suture needle is allowed to pass through a region surrounded by the suture wire, thus forming a knot at the first needle guide hole. When the suture needle enters again from the fourth needle guide hole and exits from the second needle guide hole, when the needle tip comes out, the suture wire passes clockwise in front of the needle tip, and then the suture needle is allowed to pass through a region surrounded by the suture wire, thus forming a knot at the second needle guide hole. In some implementations, the first and second needle guide holes and the third and fourth needle guide holes are distributed on the two sides of the wiring region, and the first needle guide hole and the third needle guide hole are not in a same straight line, optionally, the second needle guide hole and the fourth needle guide hole are likewise not in a same straight line. Optionally, a connecting line of the first needle guide hole and the third needle guide hole is parallel to a connecting line of the second needle guide hole and the fourth needle guide hole. When double needles are used for suture, a wiring channel is arranged near the wiring region, and the wiring channel can allow two needles connected by a suture wire to pass through. In this way, suture needles are arranged on both the two sides of the chamber, and the suture needle on one side continuously passes on one side of the wiring region of the chamber, thus forming a structure similar to locking on the sutured tendon. Of course, it can be understood that the needle on the other side also continuously passes in the wiring region on the other side, forming a structure similar to locking on the other side of the tendon. The wiring regions here can be distributed on two sides of the chamber and does not need to be symmetrically arranged, because the suture needles can independently and continuously pass in different wiring regions, separately.

In some implementations, near the wiring region, such as near the opening of the chamber, a wiring channel is arranged separately, needle threading holes are arranged at two ends of the channel, wherein the needle threading hole at one end is used for connecting suture needles at two ends by suture wires to penetrate through the chamber, allowing the suture needles to be distributed on two sides of the chamber. When suture is performed, the suture needles enter from the needle guide hole at the other end of the wiring channel, and exit from the needle guide hole on one side of the wiring region, and the one side of the wiring region is an opposite side of the needle guide hole on the channel that allows the needles to enter.

In some implementations, in the above different suture ways, suture wires are arranged on two sides of the tendon. When the ruptured tendons are connected, it is expected that the ruptured surfaces are aligned without misalignment, which is conducive to the growth of the tendons. Hence, in some implementations, independent needle guide holes are arranged on the wall of the chamber near a tendon rupture opening, and the needle guide holes are arranged on two sides of the chamber, so that the composite wires can pass through the tendons. In some implementations, when wiring channels or wiring regions are arranged on the chamber (such as the wall of the chamber), the separate needle guide holes are arranged in a staggered manner with the wiring channels or the wiring regions, so that the wiring channels or the wiring regions are distributed on two sides of the tendons, and the needle guide holes are used to allow the suture wires to be distributed in the middle of a wiring region of the wiring channels or the wiring regions on the tendon. In this way, from a cross-sectional perspective, there are suture wires in all four directions on the tendon. So, when the surfaces of the ruptured tendons are combined, the contact surfaces of the ruptured surfaces are aligned, which is conducive to the later growth or healing of the tendons.

In another aspect, the present invention provides a method for tendon suture using a suture instrument or a method for using a tendon suture instrument. The method includes providing the tendon suture instrument which includes an open chamber defined by a side wall.

In some implementations, a first wiring channel is arranged on a side wall of the chamber along a longitudinal direction of the chamber, and a second wiring channel is arranged symmetrical to the first wiring channel along a longitudinal axis of the chamber. A first needle guide hole, a second needle guide hole and a third needle guide hole are arranged sequentially on the first wiring channel, and a fourth needle guide hole, a fifth needle guide hole and a sixth needle guide hole are arranged sequentially on the second wiring channel, wherein the first needle guide hole and the fourth needle guide hole are arranged in a symmetrical communication manner, the second needle guide hole and the sixth needle guide hole are arranged in a communication manner, and the third needle guide hole and the fifth needle guide hole are arranged in a communication manner. A first suture needle and a second suture needle connected to a suture wire are provided. The method includes:

first step: the first suture needle enters from the first needle guide hole of the first wiring channel and exits from the fourth needle guide hole of the second wiring channel, so that the first suture needle is located on one side of the second wiring channel.

In some implementations, the method further includes a second step: the first suture needle enters from the fifth needle guide hole and exits from the third needle guide hole, and the second suture needle enters from the second needle guide hole and exits from the sixth needle guide hole.

In some implementations, a first wiring channel and a second wiring channel are arranged on the wall of the chamber, and a third wiring channel and a fourth wiring channel are arranged symmetrical to the first wiring channel and the second wiring channel on the wall of the chamber, wherein the first wiring channel is not in communication with the second wiring channel, and the third wiring channel is not in communication with the fourth wiring channel. In some implementations, one or more needle threading holes are arranged on the first wiring channel, the second wiring channel, the third wiring channel, and the fourth wiring channel. In some implementations, the first wiring channel, the second wiring channel, the third wiring channel, and the fourth wiring channel are arranged along a longitudinal direction of the chamber. In some implementations, the size of the needle guide hole is essentially equal to the size of the wiring channel, or the width of the wiring channel is little different from the width of the needle guide hole. In the above implementations, a method is further included as follows: allowing a suture needle to enter from a needle guide hole of the first wiring channel and exit from a needle guide hole of the fourth wiring channel, and then enter from the needle guide hole of the fourth wiring channel and exit from the needle guide hole of the second wiring channel; alternatively, allowing the suture needle enter from a needle guide hole of the third wiring channel and exit from the needle guide hole of the second wiring channel, and then enter from the needle guide hole of the second wiring channel and exit from the needle guide hole of the fourth wiring channel.

In some implementations, a first wiring channel and a second wiring channel are arranged on the same side of the wall of the chamber, and one or more needle guide holes are arranged on each wiring channel, allowing a suture needle to enter from the needle guide hole at one end of the first wiring channel and exit from the needle guide hole of the second wiring channel. In some implementations, a first wiring channel and a second wiring channel are arranged on one side of the wall of the chamber, and a first needle guide hole (e.g., an upper position) and a second needle guide hole (a lower position) are arranged on the first wiring channel. For example, at two ends of the channel, a third needle guide hole (also an upper position) and a fourth needle guide hole (a lower position) are arranged on the second wiring channel, allowing a suture needle to enter from the second needle guide hole of the first wiring channel and exit from the third needle guide hole of the second wiring channel. The method further includes allowing the suture needle to enter from the fourth needle guide hole of the second wiring channel and exit from the fifth needle guide hole (upper) of the third wiring channel. In this way, the suture wire is arranged on the surface of the tendon by means of the wiring channels, it the tendon is located in the chamber.

DETAILED DESCRIPTION OF THE INVENTION

Figure 1:
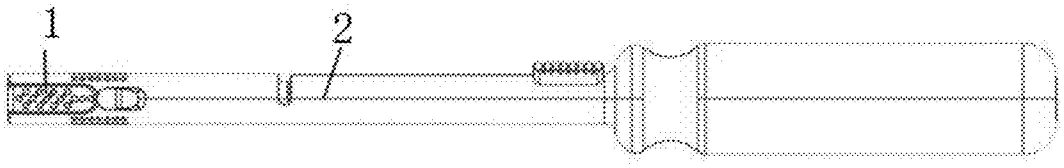
FIG. 1 is a schematic diagram of an overall three-dimensional structure of a suture instrument of the present invention.
Figure 2:
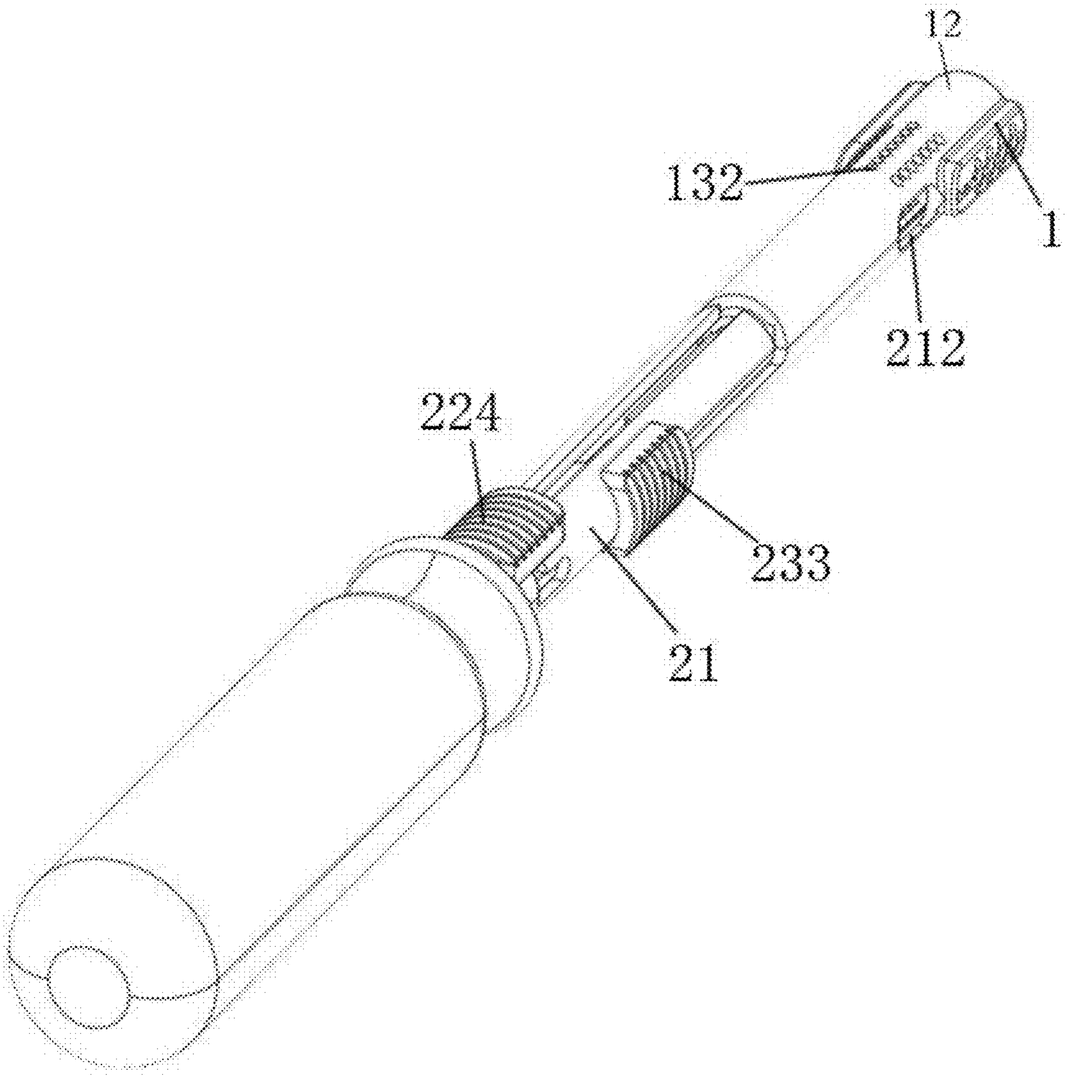
FIG. 2 is a schematic diagram of a three-dimensional structure of the suture instrument of the present invention.

In order to facilitate a better understanding of the present invention by those skilled in the art, the following will provide a clear and complete description of the technical solution in the embodiments of the present invention, in conjunction with the drawings in the embodiments of the present invention.

The commonly used current treatment for tendon rupture is surgery, through which ruptured tendons are sutured. A tendon suture instrument of the present invention is a surgical medical instrument that assists surgeons in more precise suturing of ruptured tendons. Tendon rupture, as the name suggests, refers to that there is the phenomenon of rupture at tendons. At this point, the tendon includes a rupture opening, and the surgery is to align and suture the two ends of the rupture opening.

In some implementations, the tendon suture instrument of the present invention includes a gripping element 2 and a chamber 10 having an opening 11. The chamber 10 is used for accommodating a sutured tendon tissue. The tendon tissue can enter the chamber 10 through the opening 11 of the chamber when needing to be sutured. The chamber 10 is defined by a wall 12. Wiring channels and needle guide holes are arranged on the wall 12. The gripping element 2 can place a tendon 100 in the chamber 10 or release the tendon 100 from the chamber 10. In some implementations, the gripping element 2 can allow the tendon 100 to enter the chamber 10 from the opening 11 of the chamber 10, and relatively fix the tendon 100 at a position in the chamber 10. At this point, the tendon can be sutured, for example, suture wires are arranged on the tendon. After the suture is completed, the gripping element 2 can allow the tendon 100 to exit from the chamber 10 through the opening 11, thus completing the suture of the tendon. The term "release" here can mean allowing the tendon 100 to exit from the chamber 10, or allowing the tendon 100 to detach from the gripping element 2.

Figure 3:
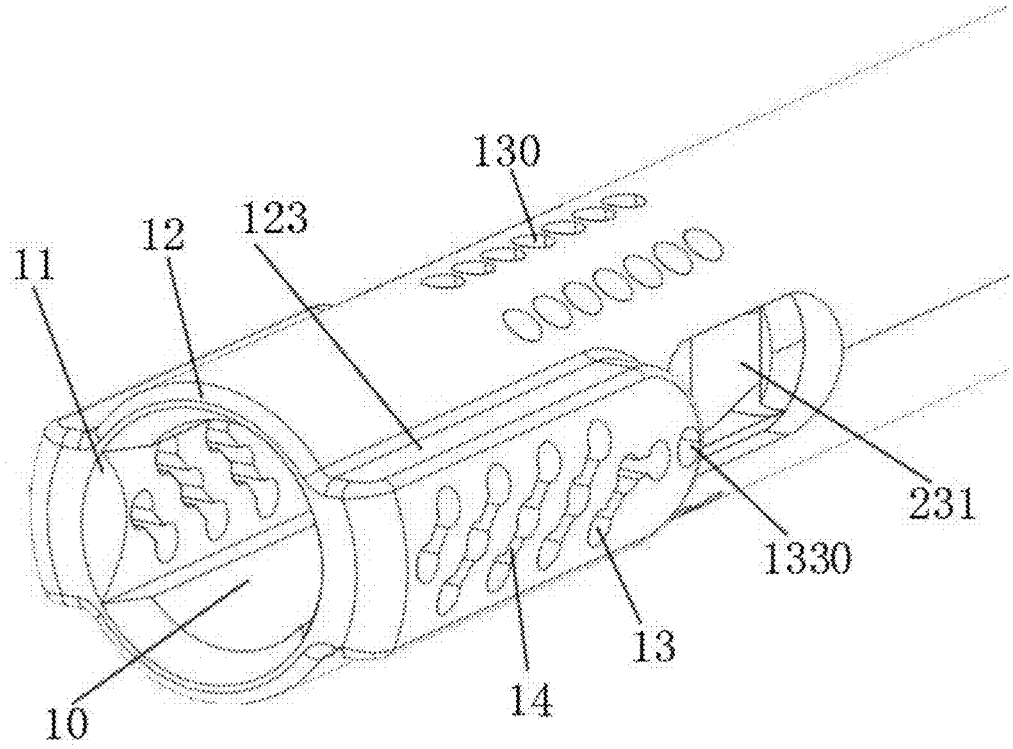
FIG. 3 is a structural schematic diagram of a guiding element of a cross weaving method of the present invention.

In some implementations, one or more, or multiple needle guide holes 13 and wiring channels 14 are arranged on the wall 12. Of course, the needle guide holes can be located in the wiring channels as part of the wiring channels. For example, wiring channels 14 in FIG. 3 each have multiple needle guide holes, two needle guide holes are distributed at two ends of the wiring channel, and another needle guide hole 133 is located in the middle of the channel. These needle guide holes are also part of the channels.

In some implementations, the needle guide holes 13 and the wiring channels 14 are arranged on the wall 12, and can guide a suture needle to suture the tendon 100. When the tendon suture instrument of the present invention is used, firstly, one end of a tendon rupture opening is gripped by the gripping element 2 and placed in the chamber 10, and at the same time, the gripping element 2 can also fix the tendon 100, ensuring that the tendon 100 will not move in the chamber 10 during suture; then the surgeon guides the movements in different ways of the suture needle through the needle guide holes 13 and the wiring channels 14 on the wall 12 to arranges a suture wire on the tendon. The suture needle is connected to a suture wire 103. By means of the movement of the suture needle and the suture wire 103 on the tendon 100, the suture wire 103 is arranged on certain parts of the tendon 100. After the arrangement is completed, the gripping element 2 releases the tendon 100. At this time, the tendon 100 can detach from the tendon suture instrument, and at this point, the tendon 100 connected to the suture wire 103 can also detach from the tendon suture instrument. The previous operation is repeated, and the same is done for the tendon at the other end. At this point, the suture wire 103 has been fixed at two ends of the tendon rupture opening. The tendon has a certain elasticity, and by pulling the suture wire 103 at the two ends, the tendon rupture openings are aligned and connected and fixed by means of the suture wire 103, thus completing the surgery.

It needs be noted that there are many methods for suture by means of the suture needle and the suture wire 103, such as a cross weaving method, a Bunnel suture method, and a running cycle suture method. In order to match or standardize these suture methods, the present invention designs and arranges needle guide holes 13 and wiring channels 14 that can correspond to these suture methods. Under the guidance of the needle guide holes 13 and the wiring channels 14, different surgeons can also perform standardized suture operations. Therefore, the present invention designs multiple types of arrangements of the needle guide holes 13 and the wiring channels 14. The tendon suture instrument of the present invention can eliminate the dependence on the operator's experience for the suture effect thereof, and with the normative guidance of the tendon suture instrument, different suture methods are used according to the different degrees of tendon rupture at different parts, thereby achieving a better tendon suture effect. In addition, the tendon suture instrument of the present invention actually requires a small surgical space and is also suitable for small-space tendon fracture end parts. The tendon suture instrument of the present invention not only reduces the difficulty of suturing tendon fracture ends during surgery, but also selects the most suitable suture method according to the actual situation, making high suture mechanical strength of the sutured tendon, thus shortening the plaster fixation cycle or eliminating the need for plaster fixation, avoiding complications such as tendon adhesion and ankylosis caused by long-term plaster fixation braking, and effectively promoting rapid tendon repair and postoperative motor function recovery of patients.

The gripping element 2 and a guiding element 1 may be integrally formed or detachable connected. The mode for detachable connection may be modes such as connection through threads, to replace the guiding element 1, thereby replacing the suture method. The following embodiments are all described using the integrated tendon suture instrument as an example. The disassembly connection mode of the detachable tendon suture instrument is the prior art and will not be repeated.

Cross Weaving Method

As shown in FIGS. 1-5, a tendon suture instrument includes a chamber 10 where a tendon 100 can be placed. One end of the chamber 10 is provided with an opening 11, and the other end thereof is connected to a gripping element 2. The gripping element 2 can stretch and retract in the chamber 10. The chamber 10 is used for accommodating a sutured tendon tissue. The tendon tissue can enter the chamber 10 through the opening 11 of the chamber 10 when needing to be sutured, so that the gripping element 2 fixes the tendon 100 in the chamber 10. In addition, the gripping element 2 can also release the tendon 100 from the chamber 10.

In some implementations, a first wiring channel 141 and a first needle guide hole 131 are arranged on a side wall 12, and the first wiring channel 141 includes the first needle guide hole 131, wherein the other side wall of the chamber 10 includes a second wiring channel 142 including a third needle guide hole 133, and the first wiring channel 141 and the second wiring channel 142 are distributed on two sides of the chamber.

The first needle guide hole 131 of the first wiring channel 141 is arranged to guide a suture needle to pass through a cross section of the chamber 10 and then exit from the third needle guide hole 133 of the second wiring channel 142; a second needle guide hole 132 is arranged on the first wiring channel 141, and the first needle guide hole 131 and the second needle guide hole 132 are distributed at two ends of the first wiring channel; the second wiring channel 142 further includes a fourth needle guide hole 134, and the third needle guide hole 133 and the fourth needle guide hole 134 are distributed at two ends of the second wiring channel 142; and the first wiring channel 141 and the second wiring channel 142 are axisymmetrically arranged along the chamber 10, wherein a third wiring channel 143 is arranged near the same side as the first wiring channel 141, a fourth wiring channel 144 is arranged near the same side as the second wiring channel 142, and a fifth needle guide hole 135 and a sixth needle guide hole 136 are arranged at two ends of the third wiring channel 143; a seventh needle guide hole 137 and an eighth needle guide hole 138 are arranged at two ends of the fourth wiring channel 144.

In some implementations, suture needles include a first suture needle 101 and a second suture needle 102, when passing into the first needle guide hole 131 of the first wiring channel 141, the first suture needle 101 can pass out of the third needle guide hole 133 of the second wiring channel 142, further, the first suture needle 101 first passes into the fourth needle guide hole 134 of the second wiring channel 142 and passes out of the sixth needle guide hole 136 of the third wiring channel 143, and then the first suture needle 101 passes into the fifth needle guide hole 135 of the third wiring channel 143 and passes out of the needle guide hole on the other side wall; the second suture needle 102 first pass into the second needle guide hole 132 of the first wiring channel 141 and passes out of the seventh needle guide hole 137 of the fourth wiring channel 144, and then the second suture needle 102 passes into the eighth needle guide hole 138 of the fourth wiring channel 144 and passes out of the needle guide hole on the other side wall.

Specifically, the needle guide holes and the wiring channels are symmetrically arranged on the side wall. Suture tools include the first suture needle 101, the second suture needle 102, and suture wires 103. The suture tools can pass out or into the wiring channels and needle guide holes multiple times. The needle guide holes are mainly used to guide the first suture needle 101 and the second suture needle 102 to needle. The wiring channels are mainly used to guide the wiring channels for threading. Under the guidance of the wiring channels and the needle guide holes, the suture wires 103 can be arranged on the tendon 100. This connection mode is standardized. Fixing needle guide holes 130 are further symmetrically arranged on the wall 12. The direction of the fixing needle guide holes 130 is different from that of the needle guide holes, and the fixing needle guide holes 130 only allows the suture needles and the suture wires to pass through the holes in a single pass. The suture wire being guided by the needle guide holes and the wiring channels can be viewed as fixing the tendon 100 in the horizontal direction, while the fixing needle guide holes 130 can be viewed as fixing the tendon 100 in the vertical direction. By means of this design, the suture wires 103 can have fixed points in both the horizontal and vertical directions. After both the two tendons 100 are fixed, they can be aligned and fixed through these suture wires 103, and can be aligned and fixed in both the horizontal and vertical directions, thereby achieving the stable weaving and suture of the ruptured tendons so as to enhance the mechanical strength of the tendons after suture.

When the tendon 100 is fixed in the chamber 10, the first suture needle 101 can pass into the tendon 100 from the first needle guide hole 131 or the third needle guide hole 133, and then the first suture needle 101 can pass out of the needle guide hole on the other side, thus completing the needle threading of the tendons. At this time, the first suture needle 101 and the second suture needle 102 are located on the two sides of the tendon 100, and the suture wires 103 pass through the tendon 100. In order to ensure that the suture needle 101 can pass vertically into the third needle guide hole 133 from the first needle guide hole 131, an extension section 123 that can increase wall thickness is further arranged on the wall 12. The extension section 123 can increase the length of the needle guide holes, thus further ensuring that the suture needle is inserted vertically into the needle guide holes. At least two needle guide holes are arranged on the wiring channel. Generally, the two needle guide holes are arranged at the two ends of the wiring channel. Preferably, the wiring channel is further provided with a third needle guide hole that is located at the center position of the wiring channel. When the wiring channel has three needle guide holes, the needle guide hole at the end is viewed as a starting needle guide hole, and the suture needle passes into the needle guide hole; the other two needle guide holes can be viewed as selective termination needle guide holes, the suture needle can selectively pass out of the needle guide holes, and this selection can be determined by the surgeon based on the size of the tendon 100. For example, for the tendon 100 having a larger width, two needle guide holes that are farther away from each other can be selected as the starting needle guide hole and the termination needle guide hole; for the tendon 100 having a smaller width, two needle guide holes that are closer to each other can be selected as the starting needle guide hole and the termination needle guide hole. Both the wiring channels and the needle guide holes can penetrate through the wall 12, the suture tools can sequentially pass into the needle guide holes and the wiring channel on one side, and pass out of the needle guide holes and the wiring channel on the other side, the suture wires 103 can also pass into the tendon 100 along the wiring channels or fit the tendon 100, finally, the suture wires connected to the suture needles can needle precisely along the wiring channels and the needle guide holes, thus completing the connection between the suture wires and the tendon 100, and ensuring that the suture wires 103 do not entangle the tendon suture instrument, thereby facilitating the smooth separation of the suture wires 103 from the tendon suture instrument after completion.

In this embodiment, in some implementations, the wiring channels on a single side are inclined and parallel in the same direction. Although the positions of the needle guide holes on the two side walls correspond one to one, from the same perspective, the wiring channels between the two side walls are inclined in opposite and staggered directions, and the two wiring channels are in a cross shape. That is to say, from one direction, the wiring channels on one side are all inclined to the right, while the wiring channels 14 on the other side are all inclined to the left.

Figure 4:
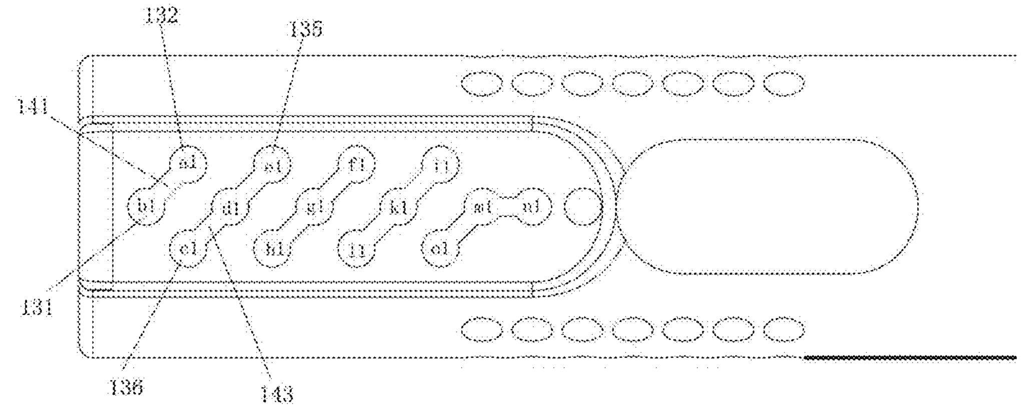
FIG. 4 is a structural schematic diagram of a cross section of the guiding element of the cross weaving method of the present invention.
Figure 4:
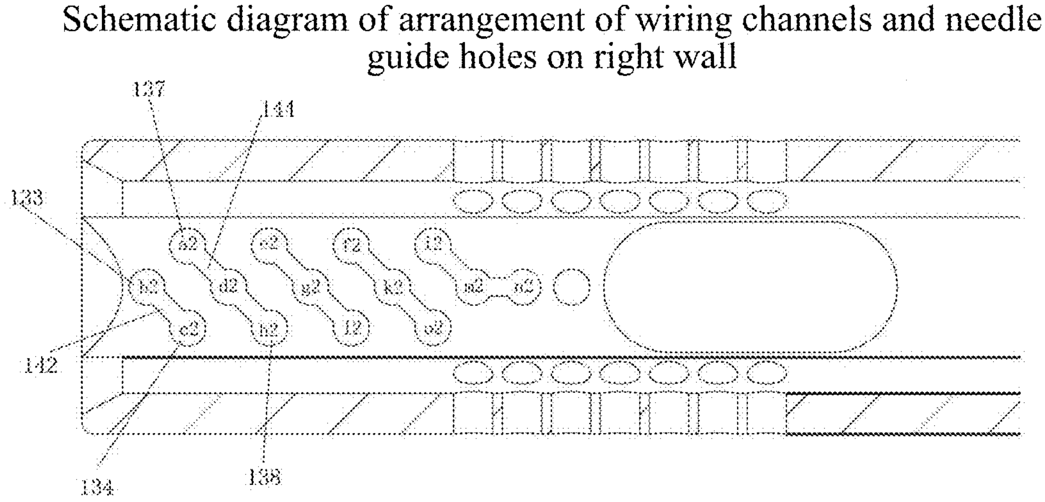
Figure 5:
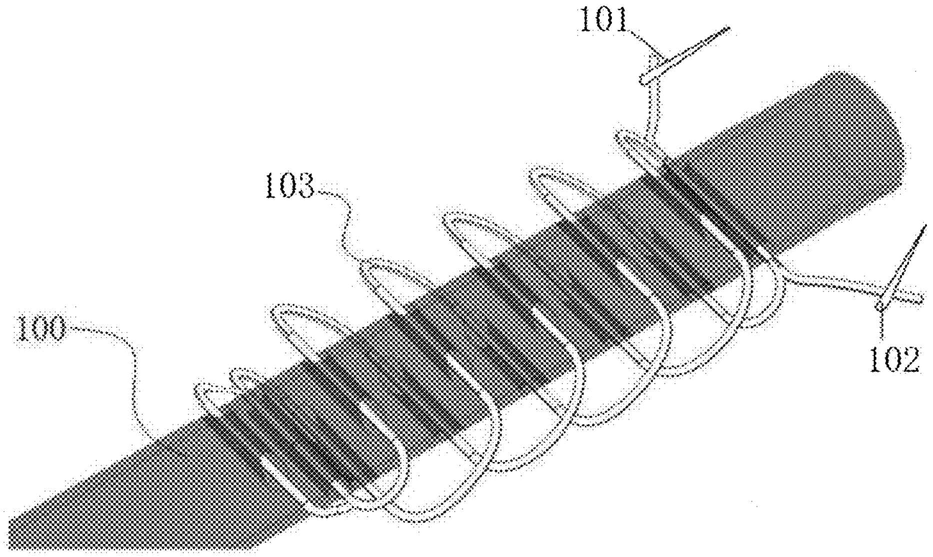
FIG. 5 is a structural schematic diagram of a tendon after suture by means of the cross weaving method of the present invention.
Figure 6:
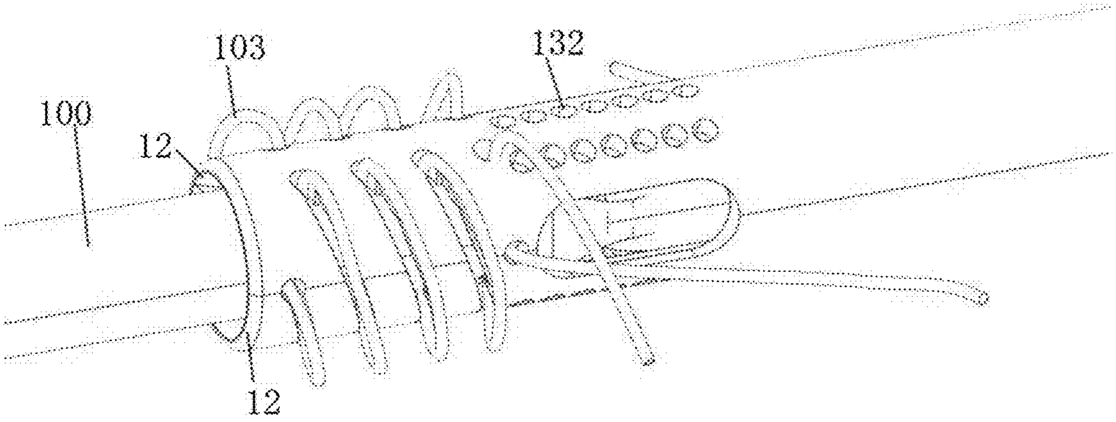
FIG. 6 is a structural schematic diagram for connection of a guiding element and a tendon of a running cycle method of the present invention.
Figure 7:
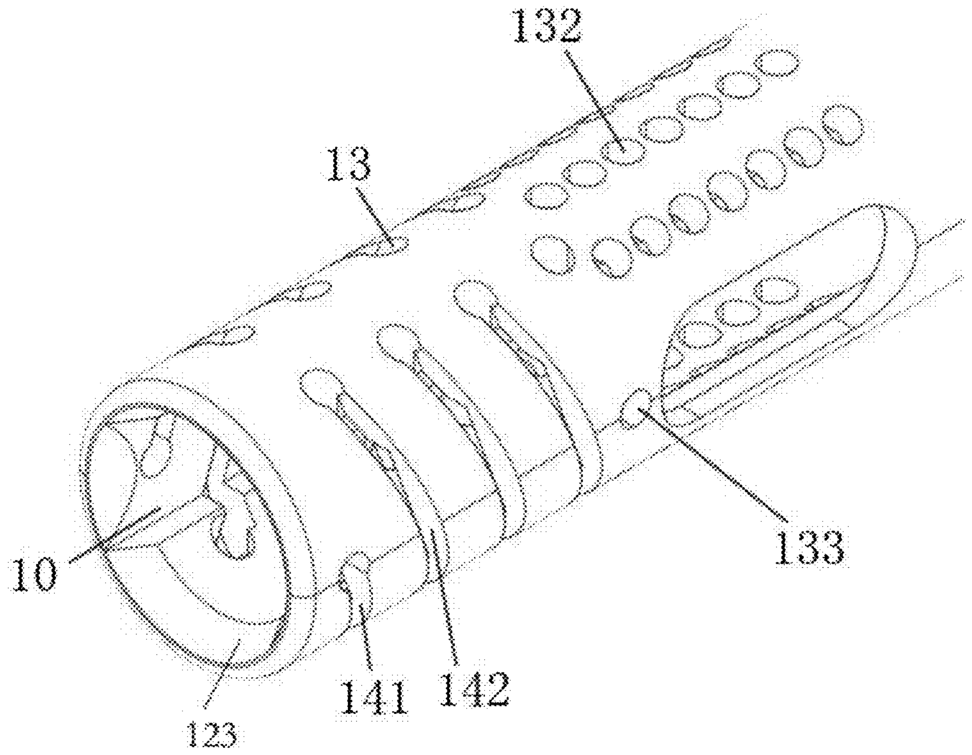
FIG. 7 is a structural schematic diagram of the guiding element of the running cycle method of the present invention.
Figure 8:
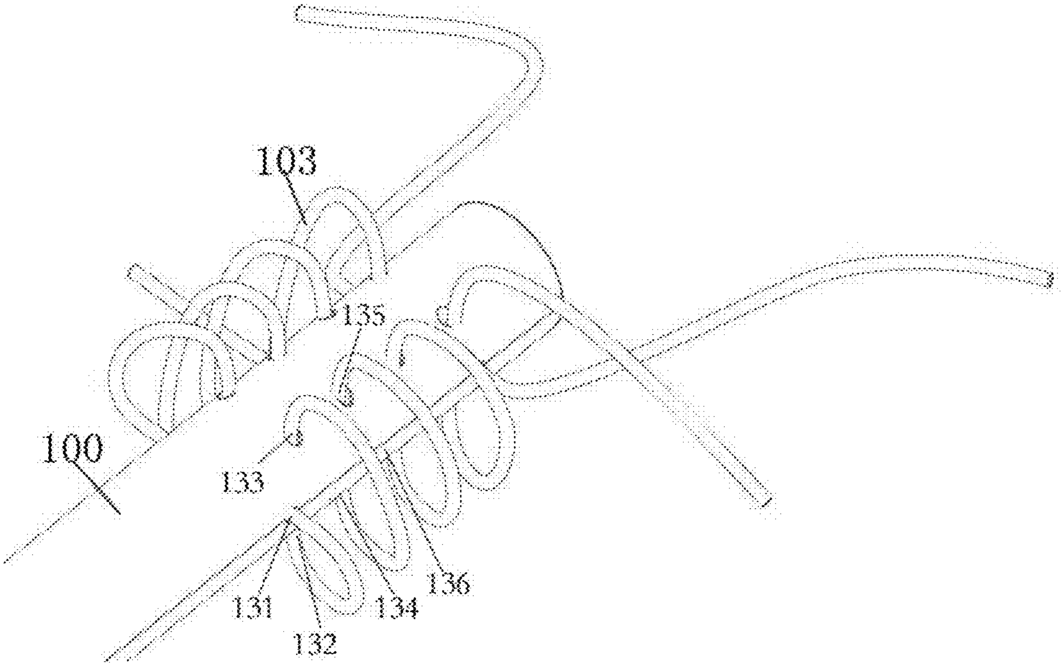
FIG. 8 is a structural schematic diagram of a tendon after suture of the running cycle method of the present invention.

The needle guide holes include a casting-on hole, a casting-off hole, and several intermediate holes, wherein the casting-on hole and the casting-off hole are located at two ends of all the needle guide holes, respectively, and both correspond to the center position of the tendon 100; the remaining intermediate holes are sequentially parallel and evenly distributed on the upper and lower sides of a connecting line between the casting-on hole and the casting-off hole, or on the same straight line as the casting-on hole and the casting-off hole. The casting-on hole is usually arranged near the opening 11, and the casting-off hole is arranged away from the opening 11, as shown in FIG. 4, a distribution schematic diagram of wiring channels 14 and needle guide holes 13 on a right wall is shown on the upper part of FIG. 4, a distribution schematic diagram of wiring channels 14 and needle guide holes 13 on the cross section of a left wall is shown on the lower part of FIG. 4, and FIG. 4 is a distribution schematic diagram of the wiring channels 14 and the needle guide holes 13 on the left wall and the right wall from the same perspective, where a1 and a2, b1 and b2, c1 and c2, d1 and d2, e1 and e2, f1 and f2, g1 and g2, h1 and h2, i1 and i2, j1 and j2, k1 and k2, l1 and l2, m1 and m2, n1 and n2, o1 and o2 correspond one to one in positions; b1 and b2 are casting-on holes, n1 and n2 are casting-off holes, and the rest are intermediate holes, d1 and d2, g1 and g2, and k1 and k2 can become casting-on holes for different suture requirements. When the mechanical requirements for some tendon sutures are not high, the surgeon can choose to suture a few less times, and the suture wire threading times is less, then the surgeon can choose the casting-on holes mentioned above.

This embodiment uses double-needle suture, that is, the two ends of one suture wire 103 are connected to the first suture needle 101 and the second suture needle 102, separately, after the tendon 100 is fixed in the chamber 10, the first suture needle 101 passes into the first needle guide hole 131 (casting-on hole b1) and passes out of the third needle guide hole 133 (b2). At this time, the first suture needle 101 and the second suture needle 102 are located on the two sides of the tendon 100, respectively, and the suture wire 103 passes through the center position of the tendon 100. The wiring channel at the casting-off position in this embodiment is L-shaped, and two needle guide holes located in the same plane can be used as selective termination needle guide holes, that is, n1 and n2 can be used as casting-off holes, and m1 and m2 can also be used as casting-off holes. Taking, for example, n1 and n2 as casting-off holes, the first suture needle 101 and the second suture needle 102 start from m1 and m2, and then pass into n1 and n2, separately, at this time, the first suture needle 101 and the second suture needle 102 are still located on the two sides of the wall 12 of the chamber, separately, and the suture wire 103 forms a circular ring at the tendon 100, making the end of the casting-off position firmer. In some cases, m1 and m2 are used directly as casting-off holes, and it is also possible that the suture needles directly pass out of m1 or m2.

Taking the tendon 100 with a smaller width as an example, two needle guide holes that are closer to each other are selected to start threading, firstly, the first suture needle 101 located on one side starts threading, and in sequence, exits from b2, enters from c2, exits from c1, enters from d1, exits from d2, enters from h2, exits from h1, enters from g1, exits from g2, enters from l2, exits from l1, enters from k1, exits from k2, enters from o2, exits from o1, enters from ml, exits from m2, enters from n2, and exits from n1, and at this point, the first suture needle 101 returns to the same side as the starting position; then, the second suture needle 102 located on the other side starts threading, and in sequence, exits from b1, enters from a1, exits from a2, enters from d2, exits from d1, enters from e1, exits from e2, enters from g2, exits from g1, enters from f1, exits from f2, enters from k2, exits from k1, enters from i1, exits from i2, enters from m2, exits from m1, enters from n1, and exits from n2, and at this point, the first suture needle 101 returns to the same side as the starting position. After the threading of both the first suture needle 101 and the second suture needle 102 are completed, the two ends of the suture wire 103 are both located on the left and right sides of the tendon 100.

Taking the tendon 100 with a larger width as an example, two needle guide holes that are farther to each other are selected to start threading, firstly, the first suture needle 101 located on one side starts threading, and in sequence, exits from b2 (a starting needle passes out of this hole), enters from c2, exits from c1, enters from e1, exits from e2, enters from l2, exits from l1, enters from i1, exits from i2, enters from m2, exits from m1, enters from n1, and exits from n2; then, the second suture needle 102 located on the other side starts threading, and in sequence, exits from b1, enters from a1, exits from a2, enters from h2, exits from h1, enters from f1, exits from f2, enters from o2, exits from o1, enters from m1, exits from m2, enters from n2, and exits from n1, and at this point, both the first suture needle 101 and the second suture needle 102 are located on the left and right sides of the tendon 100 again. It can be understood that for the needle threading holes d1, g1, k1 and m1 in the middle of the wiring channel, there is no need to let the needle pass through, so that the suture wire is arranged at the two ends of the channel. In fact, the wiring channel covers the surface of the tendon, and the suture wire is arranged on the surface of the tendon.

It can be understood that the above is a way for the suture needle to enter and exit left and right multiple times and reciprocate to arrange wires on the tendon. Of course, it can be selected one time. For example, once the starting needle starts, it can enter from c2 and exit from c1, and it is also possible that the needle on the other side exits from b2 and enters from c2. Furthermore, double needles are not necessarily required, and a single needle is also possible, that is, one needle is required to reciprocate left and right.

In summary, in this way, the threading of the suture wire in the horizontal direction is completed. In addition, reinforcing holes 1330 are further symmetrically arranged on the side wall, and are only for threading in a single pass. In addition, multiple fixing needle guide holes 130 are symmetrically arranged on the upper side wall. The direction of the fixing needle guide holes is different from that of the needle guide holes, and threading in a single pass can be performed for the multiple fixing needle guide holes 130.

That is, the suture needle with the suture wire 103 can pass into the fixing needle guide hole 130 on one side and then pass out of the fixing needle guide hole 130 on the other side corresponding thereto. Preferably, multiple rows of parallel fixing needle guide hole groups are arranged on the wall 12, and each includes multiple fixing needle guide hole groups 130 with equal spacing. Of course, multiple rows of fixing needle guide hole groups are also symmetrically arranged on the wall 12 on the other side. The fixing needle guide holes 130 are only for threading in a single pass, allowing the suture wire 103 to thread vertically.

Using the above method for threading, the threading of the suture wire is also completed on the other side of the rupture opening of the tendon 100, after the threading of the rupture openings of the two sides of the tendon 100 is all completed, the two ends of the rupture openings of the tendon 100 are aligned by pulling the suture wires 103, the suture wires 103 in both horizontal and vertical directions are connected and fixed respectively, and they can be connected by means of common knotting, thus completing tendon fracture suture.

In this embodiment, single-needle suture can also be used, only one end of one suture wire is connected to the suture needle, and the tendon 100 is fixed in the chamber 10 and then subjected to threading suture, which is different from the double-needle suture only in the threading process.

Running Cycle Method

As shown in FIGS. 6-11, a second wiring channel 142 is arranged on the same side as a first wiring channel 141 on a side wall of a chamber 10, and one or more needle guide holes are arranged on each wiring channel; a first needle guide hole 131 and a second needle guide hole 132 are arranged at two ends of the first wiring channel 141, and a third needle guide hole 133 and a fourth needle guide hole 134 are arranged at two ends of the second wiring channel 142, so that when the needle guide holes are used to guide a suture needle to move, the suture needle enters from the needle guide hole 132 at one end of the first wiring channel 141 and exits from the needle guide hole 133 of the second wiring channel 142. The first wiring channel is close to the second wiring channel, or the first wiring channel is arranged parallel to the second wiring channel, and the suture needle can pass between the first wiring channel and the second wiring channel. If there is a tendon tissue 100 in the chamber, the wiring formed in this way is similar to that shown in FIG. 8.

A first wiring channel 141 and a second wiring channel 142 are arranged on the same side on the wall of the chamber 10, a first needle guide hole 131 and a second needle guide hole 132 are arranged on the first wiring channel 141, and a third needle guide hole 133 and a fourth needle guide hole 134 are arranged on the second wiring channel 142; and when first suture is performed, a suture needle enters from the second needle guide hole 132 of the first wiring channel 141 and then exits from the third needle guide hole 133 of the second wiring channel 142. The same side on the wall 12 further includes a third wiring channel 143, a fifth needle guide hole 135 and a sixth needle guide hole 136 are arranged on the third wiring channel 143, and when suture is performed again, the suture needle enters from the fourth needle guide hole 134 of the second wiring channel 142 and exits from the fifth needle guide hole 135 of the third wiring channel 143, so that a suture wire is arranged on a surface of a tendon through the wiring channels if the tendon is located in the chamber. A first wiring channel, a second wiring channel and a third wiring channel with the same layout are also arranged on the other side of the chamber.

Multiple wiring channels and needle guide holes are symmetrically arranged on the wall 12, and each wiring channel is provided with two needle guide holes, that is, the two ends of any wiring channel 14 have only two unique needle guide holes 13; the needle guide holes 13 on the same side wall correspond coaxially one to one, and suture tools can sequentially pass into or out of the needle guide holes and wiring channels on the same side. In addition, the wiring channels on the same side wall are inclined and parallel in the same direction, and the wiring channels 14 between the two side walls are inclined in opposite and staggered directions, that is, from one direction, the wiring channels 14 on a right wall are all inclined to the right, while the wiring channels 14 on a left wall are all inclined to the left. The needle guide holes include a casting-on hole, a casting-off hole, and several intermediate holes, wherein the casting-on hole and the casting-off hole are located at two ends of all the needle guide holes, respectively, and the needle guide holes 13 all correspond to the corresponding projection position of the tendon 100. Except for the casting-on hole, the suture needle can pass into the needle guide holes 13 on any side wall and can pass out of another needle guide hole 13 corresponding thereto on the same side, thus completing the needle threading of the tendon 100. In order to ensure that the smooth insertion of the suture wire 103 into the two needle guide holes 13 on the same side, an extension section 123 is arranged on the wall 12 of the chamber near the needle guide holes 13, and the extension section 123 can increase the length of the needle guide holes, thus further ensuring that the suture needle 101 vertically passes into the needle guide holes 13. Suture using the running cycle method is performing multiple cyclic needling on the two sides of the tendon 100, thus fixing the suture wire 103 in the horizontal direction of the tendon 100.

Figure 10:
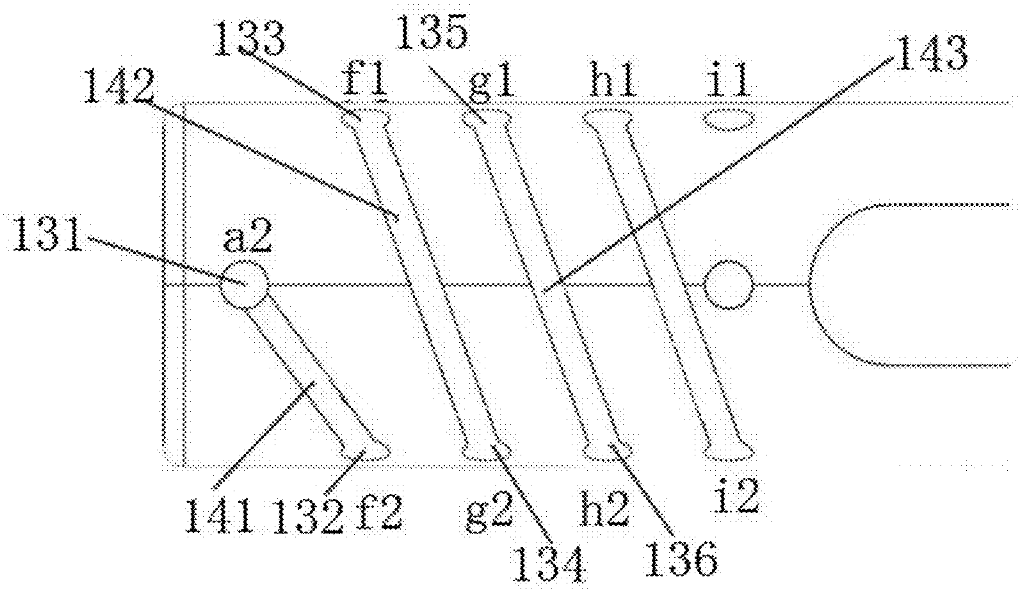
FIG. 10 is a structural schematic diagram of the wiring channels and the needle guide holes under a side-looked state of the guiding element of the running cycle method of the present invention.
Figure 10:
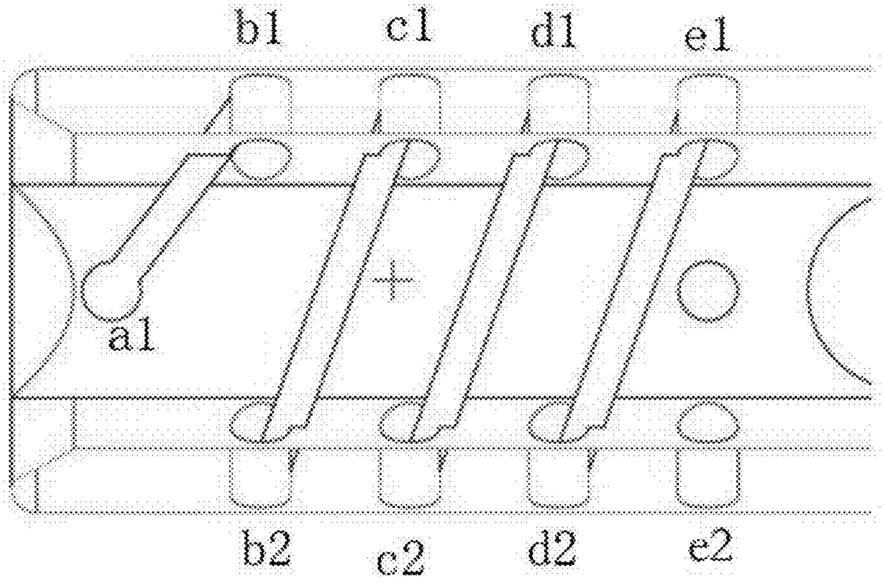
Figure 11:
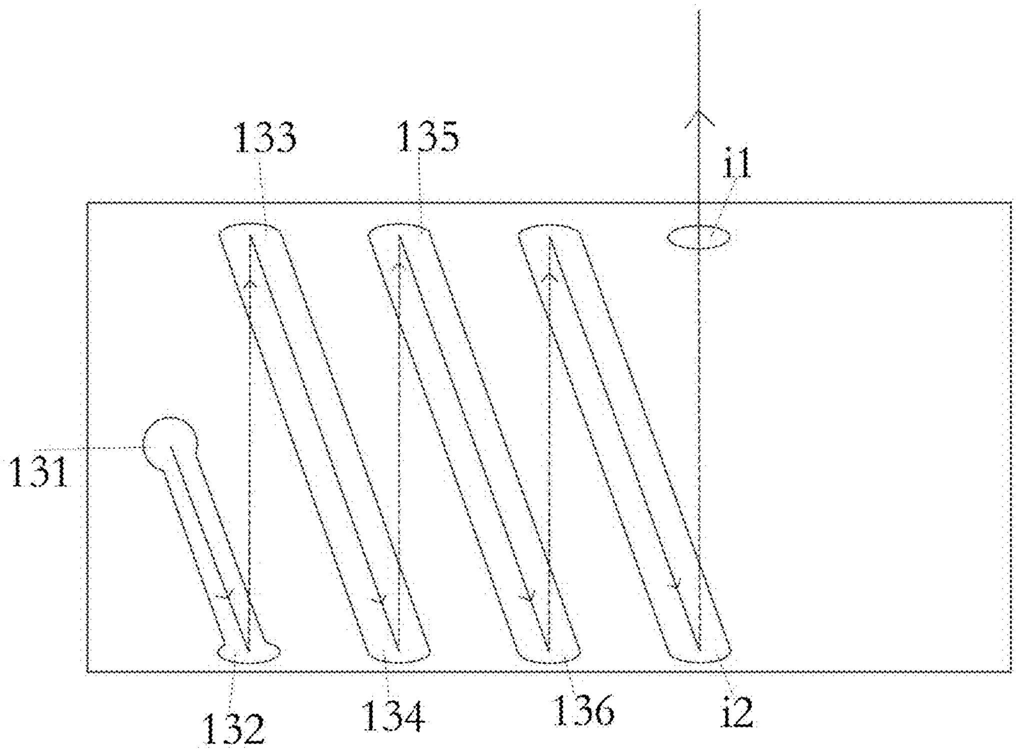
FIG. 11 is a structural schematic diagram of a needling effect of the running cycle method of the present invention.

Specifically, FIG. 10 and FIG. 11 are distribution schematic diagrams of wiring channels 14 and needle guide holes 13 on two side walls from the same perspective. In this embodiment, double-needle suture can be used, and after the tendon 100 is fixed in the chamber 10, the first suture needle 101 starts casting-on from the casting-on hole a1 or a2 of the wall 12. After casting-on, the suture wire 103 passes out of a1 and a2 (first needle guide holes), and the suture wire 103 that passes out of a1 and a2 (first needle guide holes) is in a horizontal state. The first suture needle and the second suture needle are located on the two sides of the tendon, respectively. The first suture needle 101 starts from a2 (first needle guide hole 131), and in sequence, enters from f2 (second needle guide hole 132), exits from f1 (third needle guide hole 133), enters from g2 (fourth needle guide hole 134), exits from g1 (fifth needle guide hole 135), enters from h2 (sixth needle guide hole 136), exits from h1, enters from i2, and exits from i1, i1 is a casting-off hole, and the casting-off hole i1 is an independent hole. A needle suture line 102 formed by this running needling method is in a vertical state. Similarly, the suture needle 101 near the other side wall, starts from a1, and in sequence, enters from b1, exits from b2, enters from c1, exits from c2, enters from d1, exits from d2, enters from e1, and exits from e2. e2 is a casting-off hole, and the casting-off hole e2 is an independent hole. A needle suture line 102 formed by this running needling method is also in a vertical state (as shown in FIG. 11). From FIG. 11, it can be seen that the dotted suture line is located inside the tendon, while the solid line is arranged on the surface of the tendon, which can be seen through the wiring channels.

In this embodiment, single-needle suture can also be used, only one end of one suture wire 103 is connected to the suture needle 101, and after the tendon 100 is fixed in the chamber 10, the suture needle 101 starting casting-on from e2 or i1, which is different from the double-needle suture only in the threading process.

The wall 12 of the present invention is further provided with reinforcing holes 133 and fixing needle guide holes 132, whose arrangement position and function are the same as the reinforcing holes 133 and the fixing needle guide holes 132 arranged on the guiding element of the cross weaving method, so they will not be repeated. The only difference between this embodiment and the guide element embodiment of the cross weaving method is the arrangement and layout of the needle guide holes 13 and the wiring channels 14, and everything else is the same, so they will not be repeated.

Running Locking Suture Method

As shown in FIGS. 12-16, one end of a chamber 10 is provided with an opening 11. The chamber 10 is used for accommodating a sutured tendon tissue. The tendon tissue can enter the chamber through the opening of the chamber when needing to be sutured. The chamber 10 is defined by a wall 12, and a wiring region 16 is arranged on the wall, wherein one or more needle guide holes are arranged on the wiring region. The needle guide holes are arranged on two sides of the wiring region. The wiring region is all missing regions of a side wall of the chamber. The wiring region is located on one side of the chamber 10, one or two or more needle guide holes (f1, g1, and h1) are arranged on one side of the wiring region along a longitudinal direction of the chamber, and one or two or more needle guide holes (g2, h2, and i2) are correspondingly arranged on the other side or edge of the wiring region. When a suture needle is allowed to pass out of f1 from the needle guide hole on one side of the wiring region, a suture wire is allowed to surround a needle head one round, and then the needle head is allowed to pass through a region formed by the suture wire. The suture wire surrounds the needle head in a clockwise or counterclockwise direction.

Figure 12:
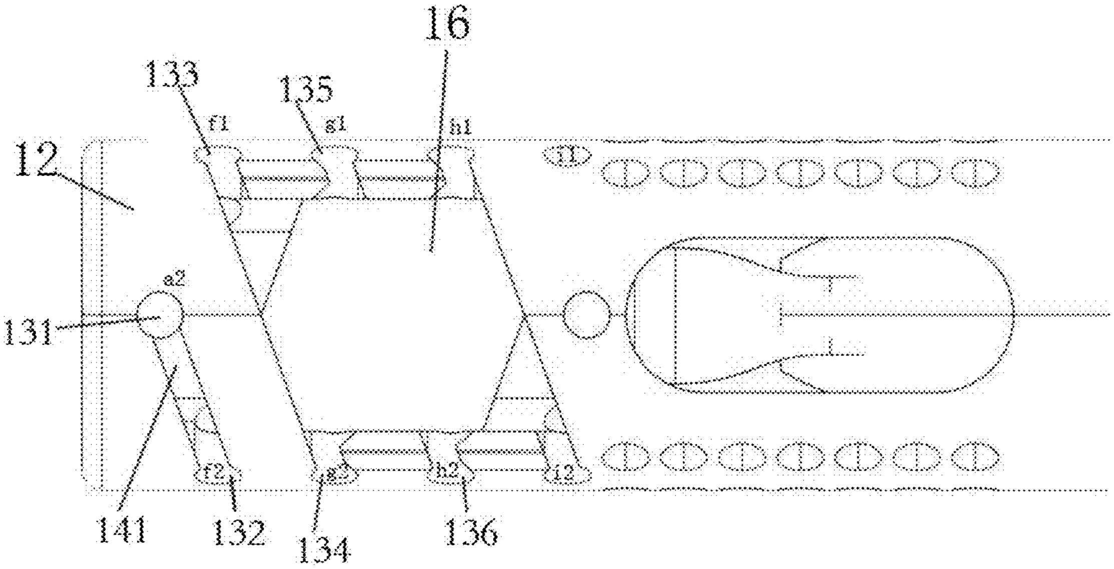
FIG. 12 is a structural schematic diagram of a front view of a guiding element of a running locking suture method of the present invention.
Figure 13:
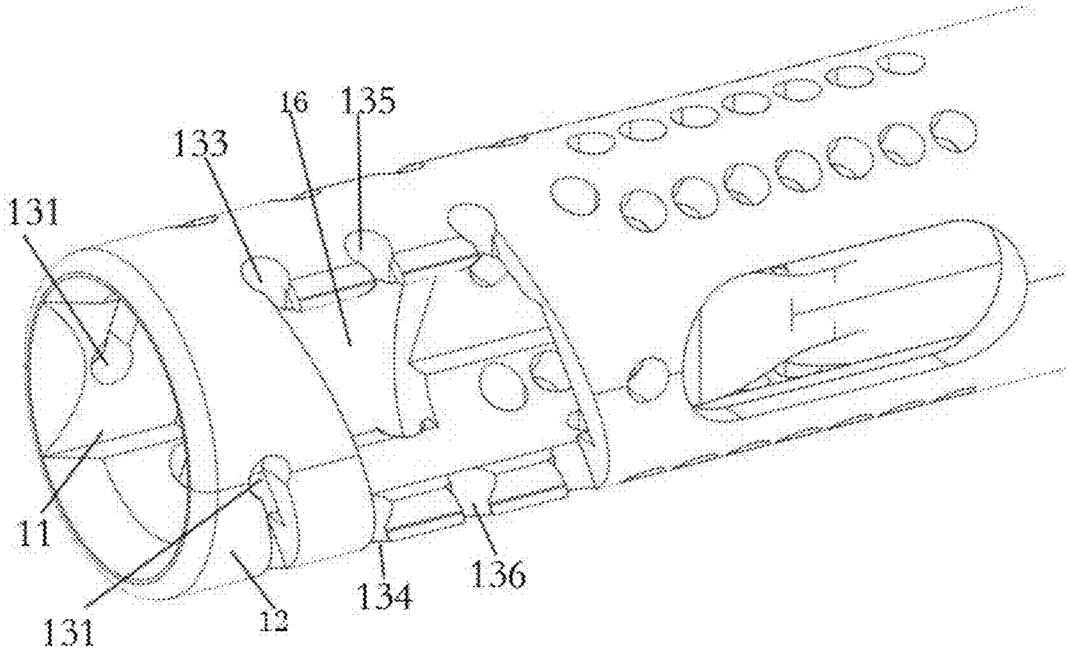
FIG. 13 is a schematic diagram of a three-dimensional structure of the guiding element of the running locking suture method of the present invention.
Figure 14:
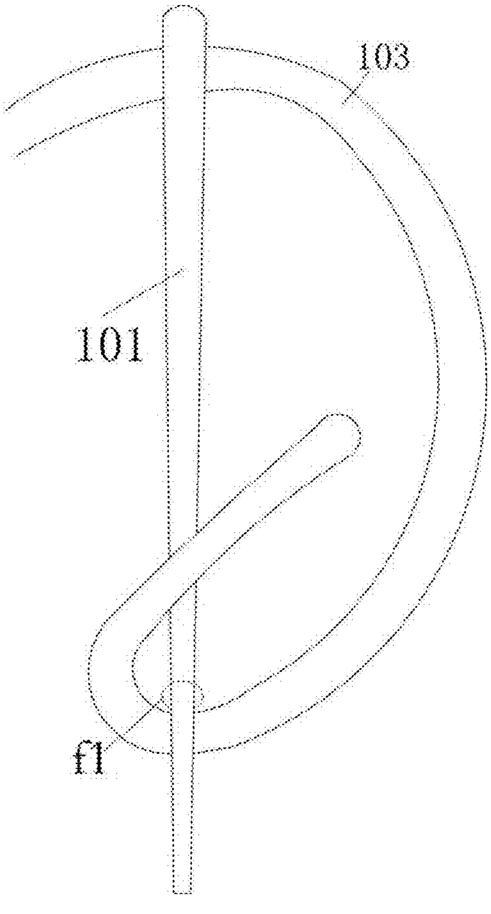
FIG. 14 is a structural schematic diagram of a needling way of a suture needle and a partition wire of the running locking suture method of the present invention.

Taking single-side needling as an example, as shown in FIG. 12, a first wiring channel 141 is included, and a first needle guide hole 131 and a second needle guide hole 132 are arranged at two ends of the first wiring channel 141; a wiring region 16 is arranged near the first wiring channel 141, a third needle guide hole 133, a fourth needle guide hole 134, a fifth needle guide hole 135 and a sixth needle guide hole 136 are arranged at edge positions of the wiring region 16, the third and fourth needle guide holes and the fifth and sixth needle guide holes are distributed on the two sides of the wiring region, and the third needle guide hole and the fourth needle guide hole are not in a same straight line, or the fifth needle guide hole and the sixth needle guide hole are likewise not in a same straight line; alternatively, a connecting line of the third needle guide hole and the fifth needle guide hole is parallel to a connecting line of the fourth needle guide hole and the sixth needle guide hole.

Figure 15:
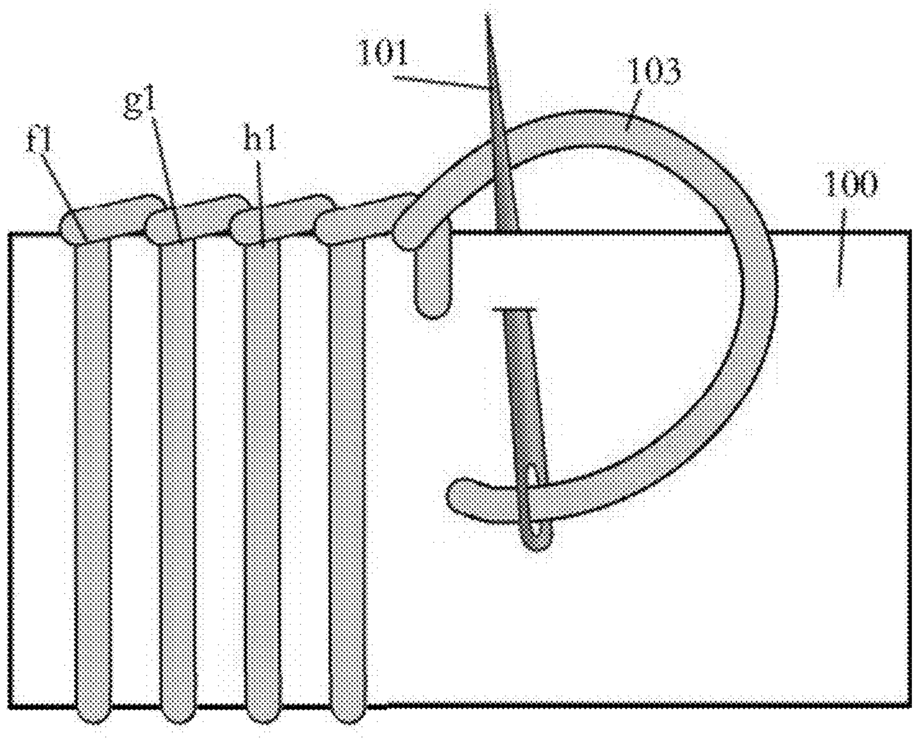
FIG. 15 is a structural schematic diagram of a tendon suture effect of the running locking suture method of the present invention.
Figure 16:
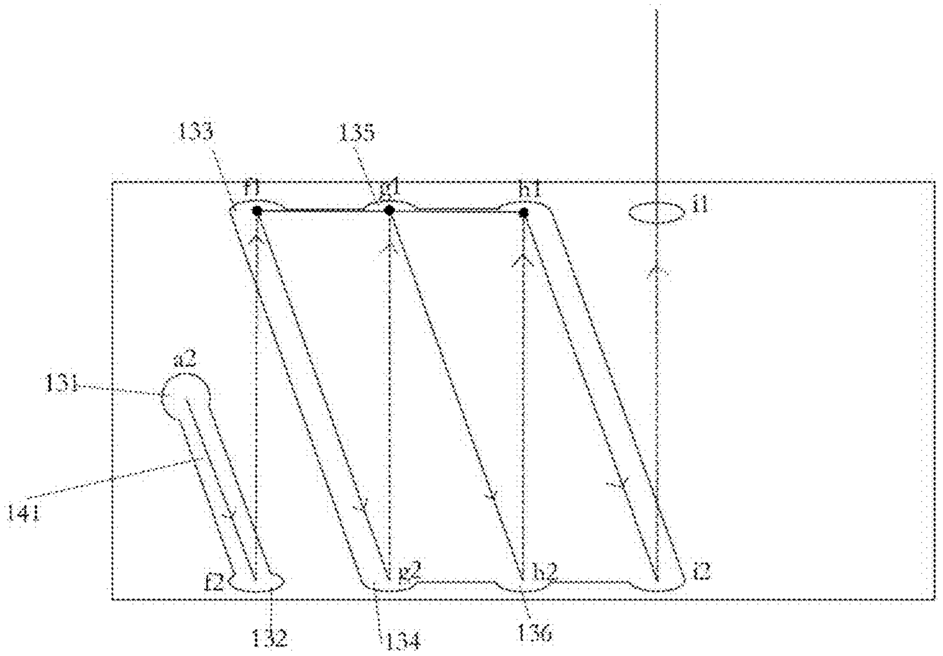
FIG. 16 is a structural schematic diagram of a needling effect of the guiding element of the running locking suture method of the present invention.
Figure 17:
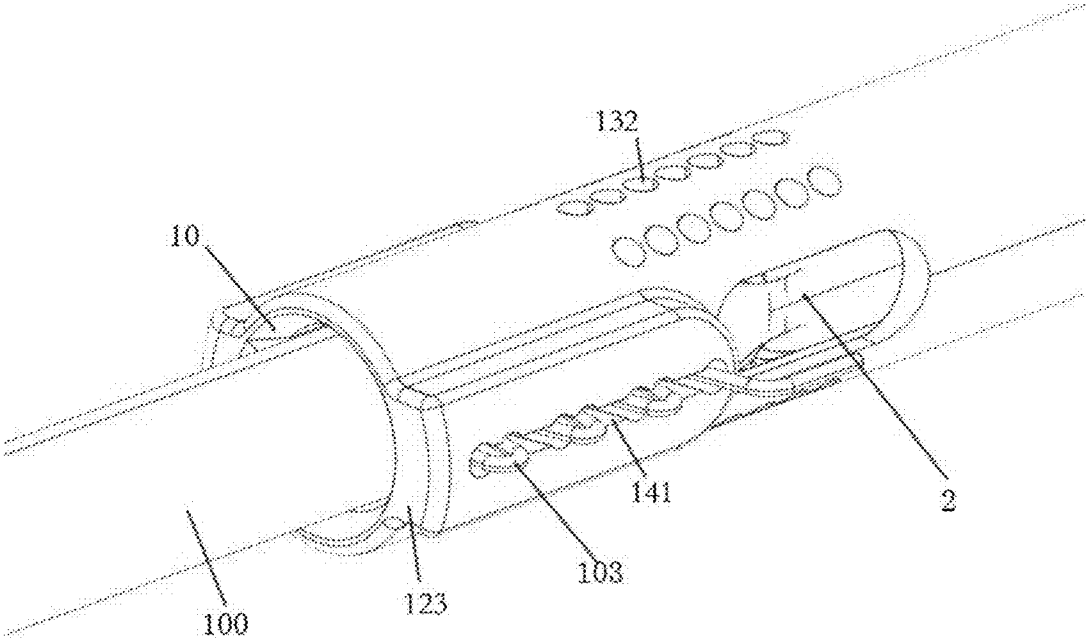
FIG. 17 is a structural schematic diagram of a guiding element and a tendon of a Bunnel suture method of the present invention.
Figure 18:
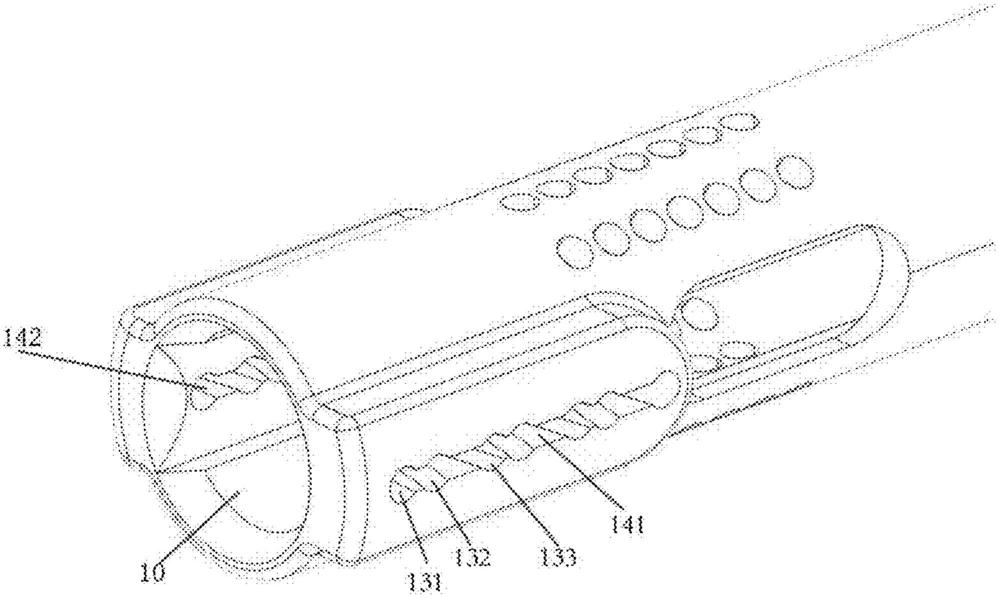
FIG. 18 is a structural schematic diagram of the guiding element of the Bunnel suture method of the present invention.

When suture is performed using the suture needle, the suture needle exits from the first needle guide hole 131 (a2), enters from the second needle guide hole 132 (f2), and then exits from the third needle guide hole 133 (f1), when a needle tip comes out, the suture wire passes clockwise in front of the needle tip, and then the suture needle is allowed to pass through a region surrounded by the suture wire, thus forming a knot at the third needle guide hole 133. Then, the suture needle enters from the fourth needle guide hole 134 (g2), and exits from the fifth needle guide hole 135 (g1), at this point, the previous knotting method is repeated, when the needle tip comes out, the suture wire passes clockwise in front of the needle tip, and then the suture needle is allowed to pass through a region surrounded by the suture wire, thus also forming a knot at the fifth needle guide hole 135. By repeating this threading back and forth, a threading pattern as shown in FIG. 15 can be formed. Of course, such wiring channels and wiring regions are also arranged on the other side of the chamber 10, which will not be repeated again.

Figure 9:
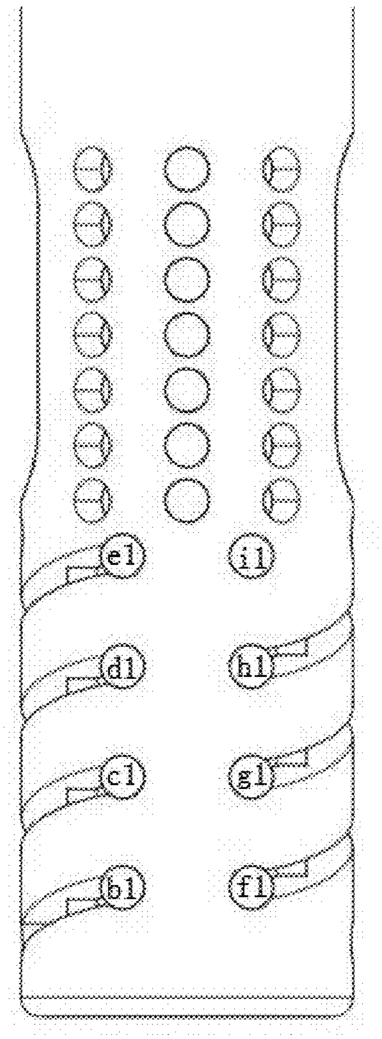
FIG. 9 is a structural schematic diagram of wiring channels and needle guide holes under an overlooked state of the guiding element of the running cycle method of the present invention.
Figure 9:
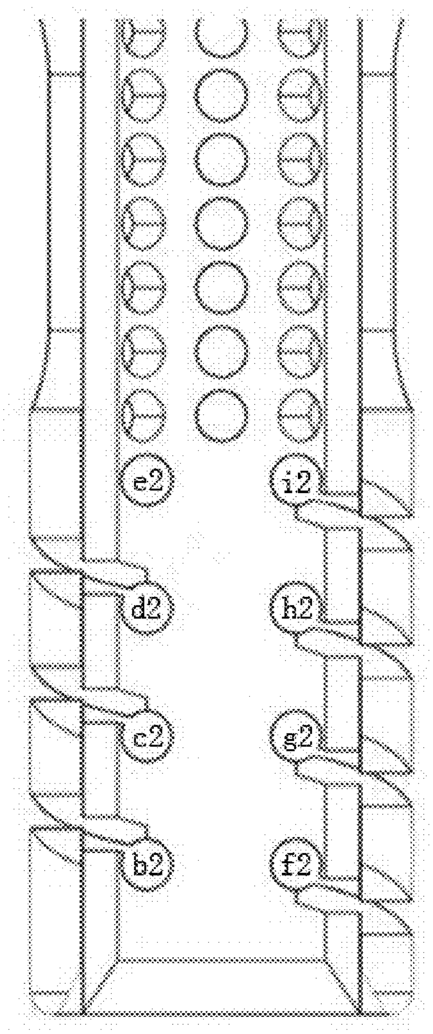

The guiding element in this embodiment differs from the guiding element in the running cycle method in structure only in a wire guiding region 15, which can be viewed as a hollow region formed by several wiring channels 14 for locking suture, its needling method and principle are the same as those of the guiding element in the running cycle method, and the same part will not be repeated. Compared with the needling method of the guiding element in the running cycle method, this embodiment has an additional step of locking, that is, the needling method is different. As shown in FIGS. 9-10, when the suture needle 101 passes out from g2 to g1, the guiding element in the running cycle method directly pulls out the suture needle 101 and the suture wire 103, the suture wire 103 is located on the left side of the suture needle 101, at this point, the suture wire 103 just passes out of the wiring channel 14. However, in this embodiment, as shown in FIGS. 12-16, when the suture needle is just inserted between g2 and g1, the suture wire passes to the right side of the suture needle 101, and the suture needle 101 and the suture wire 103 are pulled again, thus achieving a locking effect, and this process is repeated. Compared with the running cycle method, the running locking suture method is firmer and more sturdy. FIG. 15 is an effect diagram of suture using the running locking suture method.

Suitable for Bunnel Suture Method

As shown in FIGS. 17-20, a first wiring channel 141 is arranged on a side wall of the chamber 10 along a longitudinal direction of the chamber, and a second wiring channel 142 is arranged symmetrical to the first wiring channel 141 along a longitudinal axis of the chamber 10, alternatively, both the first wiring channel 141 and the second wiring channel 142 are arranged along the longitudinal direction of the chamber 10 and distributed on two sides of a central axis of the chamber. A first needle guide hole 131, a second needle guide hole 132 and a third needle guide hole 133 are arranged sequentially on the first wiring channel, and a fourth needle guide hole 134, a fifth needle guide hole 135 and a sixth needle guide hole 136 are arranged sequentially on the second wiring channel 142, wherein the first needle guide hole 131 and the fourth needle guide hole 134 are arranged in a symmetrical communication manner, the second needle guide hole 132 and the sixth needle guide hole 136 are arranged in a communication manner, and the third needle guide hole 133 and the fifth needle guide hole 135 are arranged in a communication manner. When a first suture needle and a second suture needle connected to a suture wire are used for tendon suture, the first suture needle 101 can enter from the first needle guide hole 131 of the first wiring channel 141 and exit from the fourth needle guide hole of the second wiring channel 142, so that the first suture needle 101 is located on one side of the second wiring channel 142, and the second suture needle 102 is distributed on the other side of the first wiring channel; the first suture needle 101 can enter from the fifth needle guide hole 135, exit from the third needle guide hole 133, the second suture needle 102 enters from the second needle guide hole 132 and exits from the sixth needle guide hole 136, and the suture wire is arranged on a tendon in a cross manner if the tendon tissue is contained in the chamber.

Specifically, the wall 12 is a cylindrical chamber 10, and extension sections 123 that can increase wall thickness are further arranged on the left and right side walls, wiring channels are symmetrically arranged on the extension sections 123, and the wiring channels on the two side walls are located on the same horizontal plane. The wiring channels 14 are in a straight line shape, and are provided with multiple needle guide holes, the needle guide holes on the two side walls correspond coaxially one to one, suture tools can sequentially pass into the needle guide holes on the left side wall and pass out of the needle guide holes on the right side wall, and two adjacent needle guide holes on the same side wall are arranged in a staggered manner, that is, the threading mode of the suture wire 103 presents a criss-cross shape. The needle guide holes are arranged on the wiring channels at equal intervals. The suture tools can pass out or into the wiring channels and the needle guide holes in sequence. The suture tools mainly allow the suture wire to be fixed in the horizontal direction of the tendon 100. Fixing needle guide holes 132 are symmetrically arranged on the upper and lower walls. The fixing needle guide holes 132 only allow the suture needle and the suture wire to pass through the holes in a single pass, making the suture wire 103 fixed in the vertical direction of the tendon 100. A wiring channel is arranged at the center position of the side wall, and the wiring channel 14 is also in an overlap relationship with the projection of the center position of the tendon 100. The threading position of the Bunnel suture method is located in the central region of the tendon 100.

Figure 19:
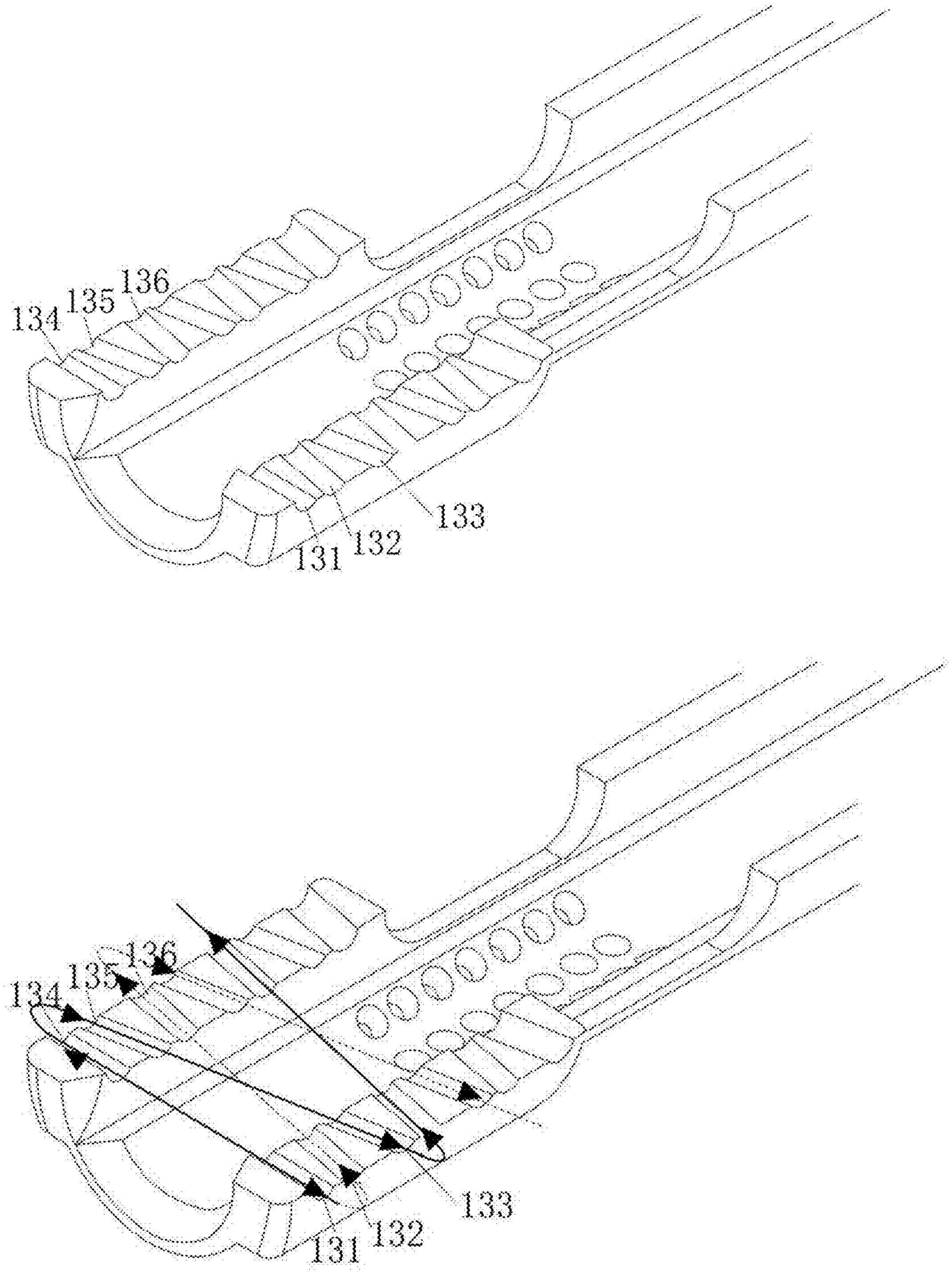
FIG. 19 is a structural schematic diagram of a cross section of the guiding element of the Bunnel suture method of the present invention.
Figure 20:
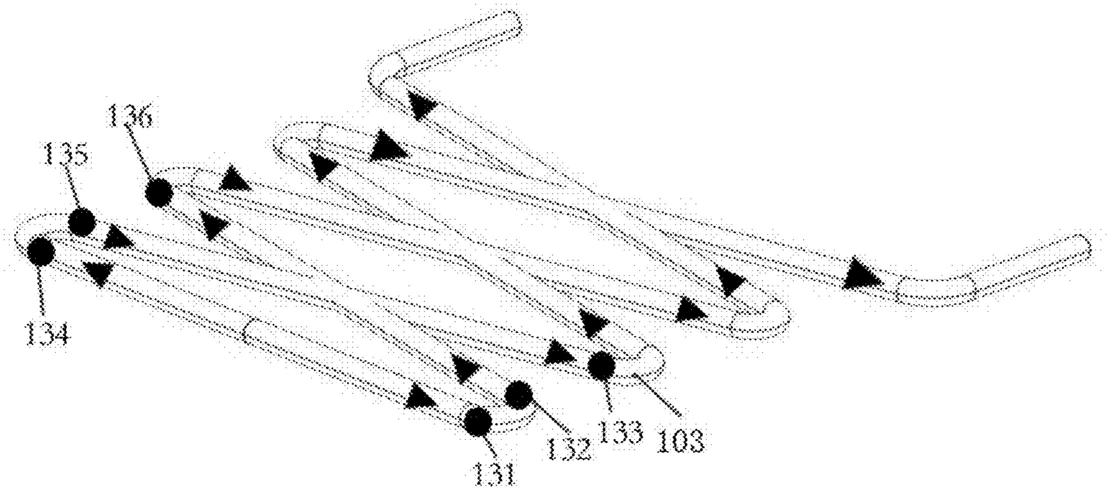
FIG. 20 is a structural schematic diagram of a suture wire after suture of the Bunnel suture method of the present invention.
Figure 21:
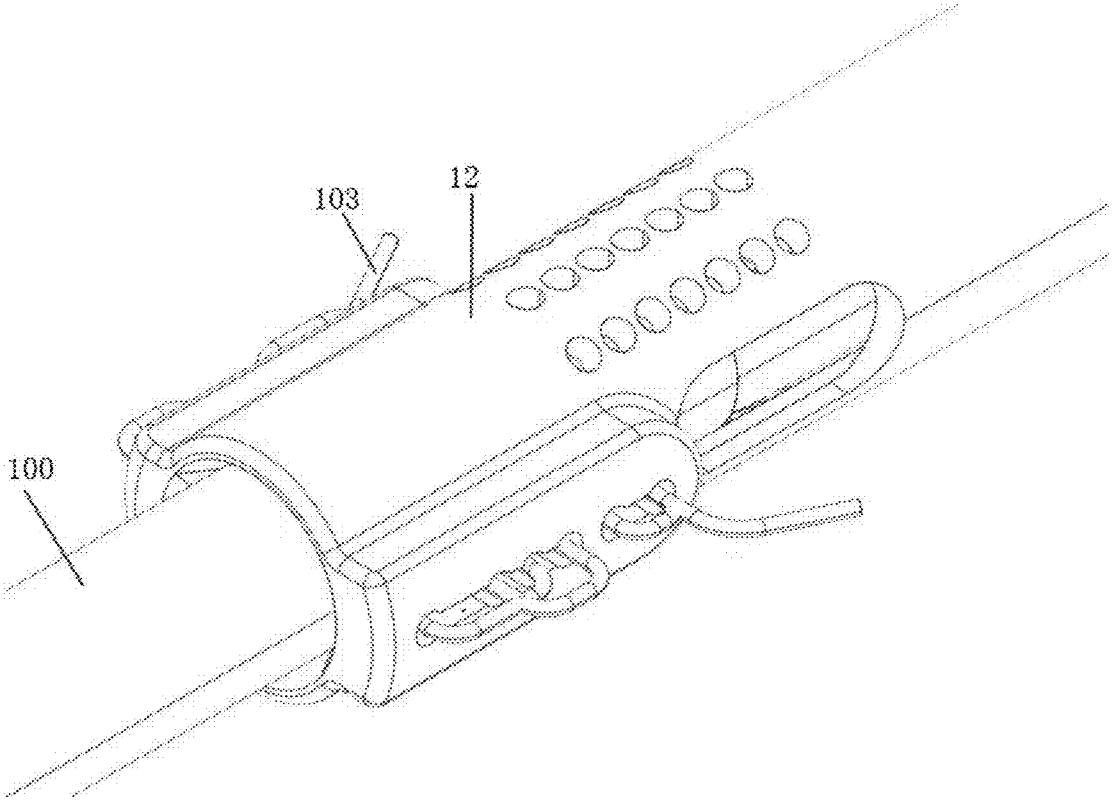
FIG. 21 is a structural schematic diagram of a guiding element and a tendon of an improved Bunnel suture method of the present invention.

As shown in FIG. 19, the needle guide holes include a casting-on hole, a casting-off hole, and several intermediate holes, the casting-on hole is perpendicular to the wiring channel, and the other adjacent needle guide holes have a certain included angle; the two adjacent intermediate holes are inclined in opposite directions. In this embodiment, double-needle suture can be used, the first suture needle 101 passes into the first needle guide hole 131 of the first wiring channel 141 and passes out of the fourth needle hole of the second wiring channel 142. At this time, the first suture needle 101 is located on one side of the second wiring channel, while the second suture needle is located on one side of the first wiring channel. Then, the first suture needle 101 starts to pass into the fifth needle guide hole 135 and passes out of the third needle guide hole; the second suture needle passes into the second needle guide hole and passes out of the sixth needle guide hole, and at this point, the suture wire forms X-shaped threading in the tendon. FIG. 20 is an effect diagram of suture by means of the guiding element of the Bunnel suture method, with a suture wire 103 presenting X-shaped threading.

Improved Bunnel Suture Method

In this embodiment, as shown in FIGS. 21-24, compared with the guiding element of the Bunnel suture method, this embodiment has the only differences that a partition is arranged on the wiring channel, and multiple needle guide holes are parallel to each other on the wiring channel. In this embodiment, wiring channels shaped like a straight line are also symmetrically arranged on the wall 12. A partition 16 is arranged on the wiring channels. Multiple needle guide holes are arranged on the wiring channels. The needle guide holes on the two side walls correspond coaxially one to one. The multiple needle guide holes are parallel to each other. Suture tools can sequentially pass into the needle guide holes on one side, and pass out of the needle guide holes on the other side.

Specifically, a second wiring channel 142 is arranged the same side wall as a first wiring channel 141 on the wall 12 of the chamber 10, and a third wiring channel 143 and a fourth wiring channel 144 are arranged symmetrical to the first wiring channel 141 and the second wiring channel 142 on the wall of the chamber, wherein the first wiring channel 141 is not in communication with the second wiring channel 142, and the third wiring channel 143 is not in communication with the fourth wiring channel 144. A length of the first wiring channel 141 is less than that of the second wiring channel 142, alternatively, a length of the third wiring channel 143 is greater than that of the fourth wiring channel 144. A projection of the first wiring channel 141 is located in or on the third wiring channel, or the length of the first wiring channel 141 is less than that of the third wiring channel; or a length of the fourth wiring channel is less than that of the second wiring channel. One or more needle guide holes are arranged on the first wiring channel, the second wiring channel, the third wiring channel, and the fourth wiring channel. The first wiring channel, the second wiring channel, the third wiring channel, and the fourth wiring channel are arranged along a longitudinal direction of the chamber.

Figure 22:
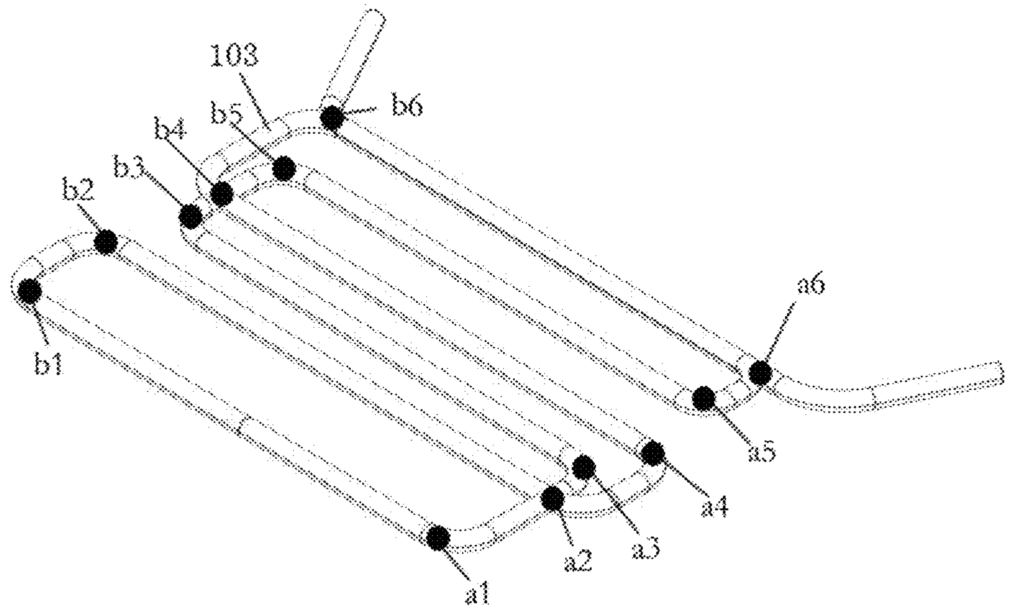
FIG. 22 is a structural schematic diagram of a suture wire after suture of the improved Bunnel suture method of the present invention.
Figure 23:
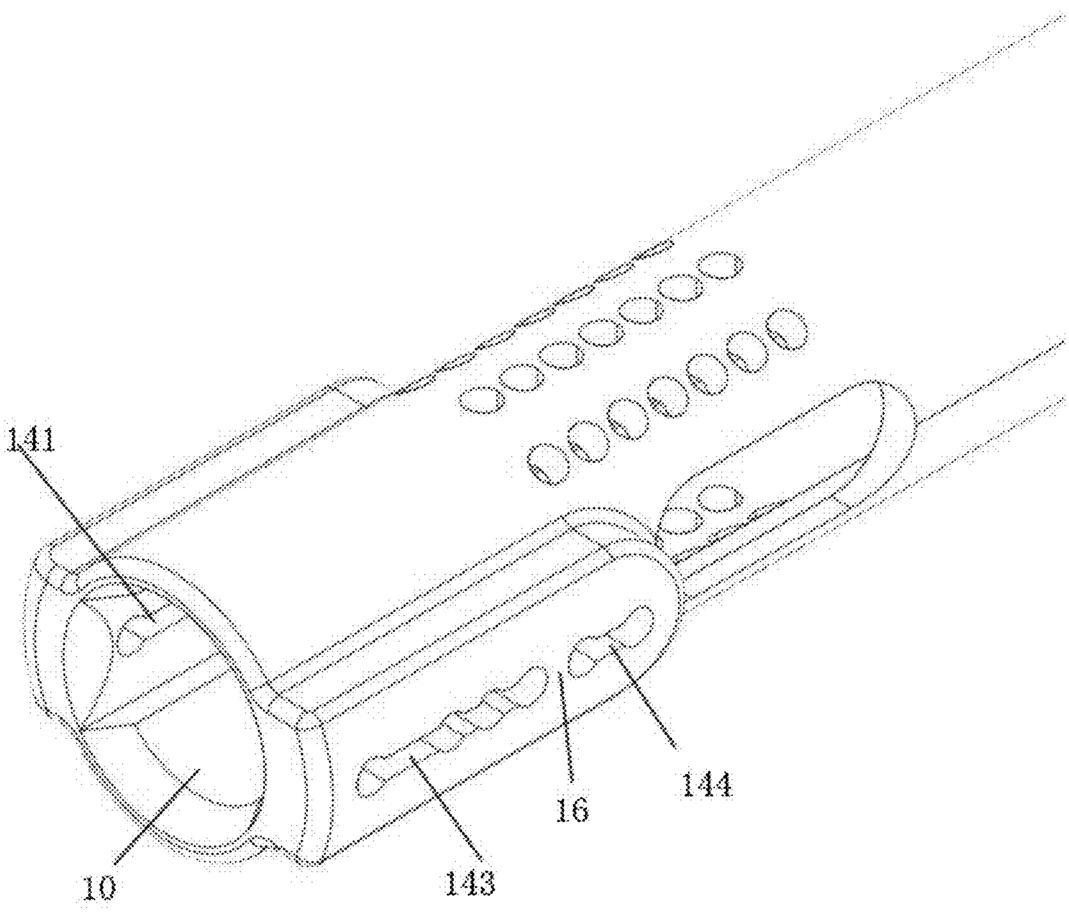
FIG. 23 is a structural schematic diagram of the guiding element of the improved Bunnel suture method of the present invention.
Figure 24:
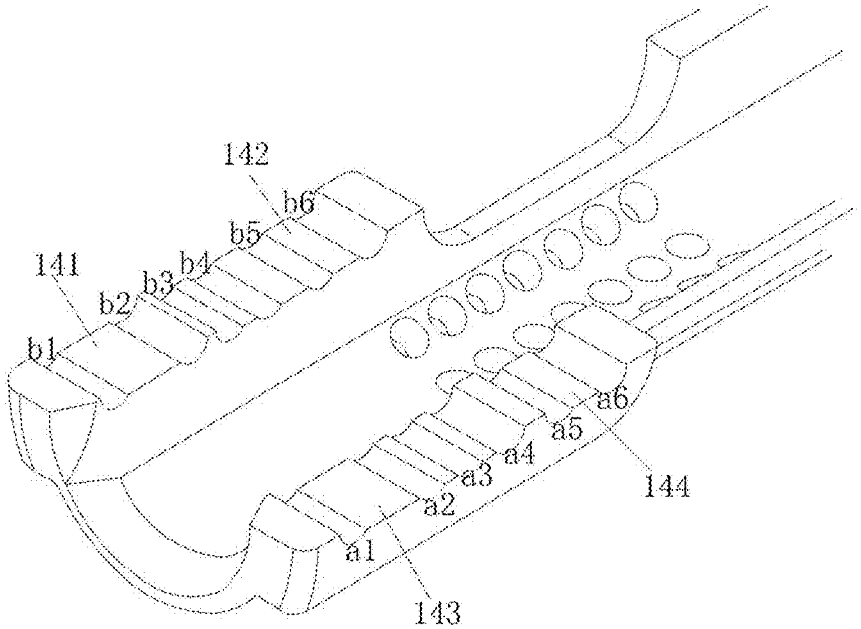
FIG. 24 is a structural schematic diagram of a cross section of the guiding element of the improved Bunnel suture method of the present invention.
Figure 25:
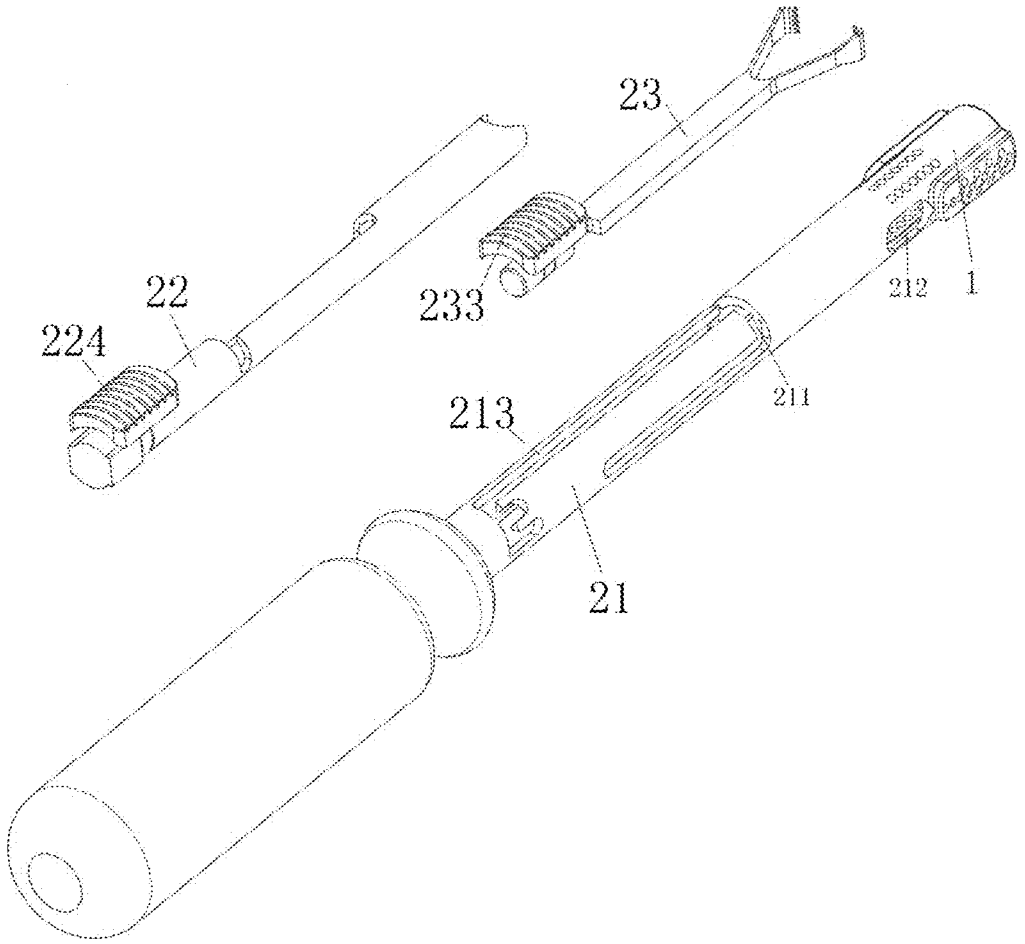
FIG. 25 is a structural schematic diagram of disassembly of a gripping element of the present invention.
Figure 26:
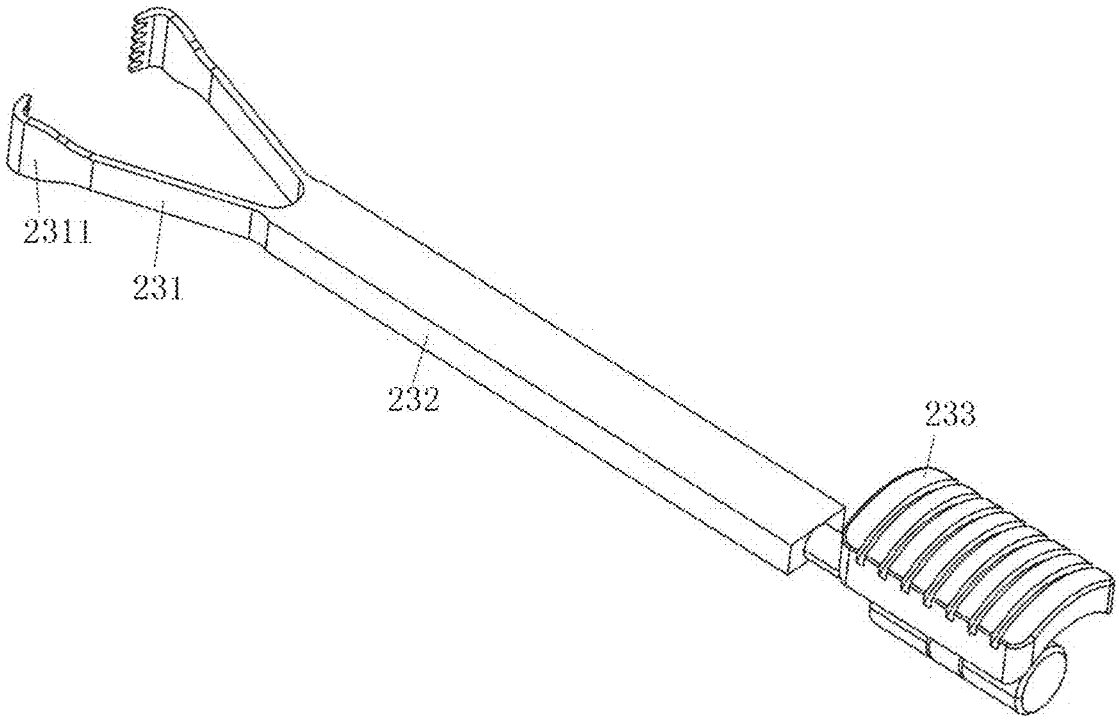
FIG. 26 is a structural schematic diagram I of a clamping rod of the present invention.
Figure 27:
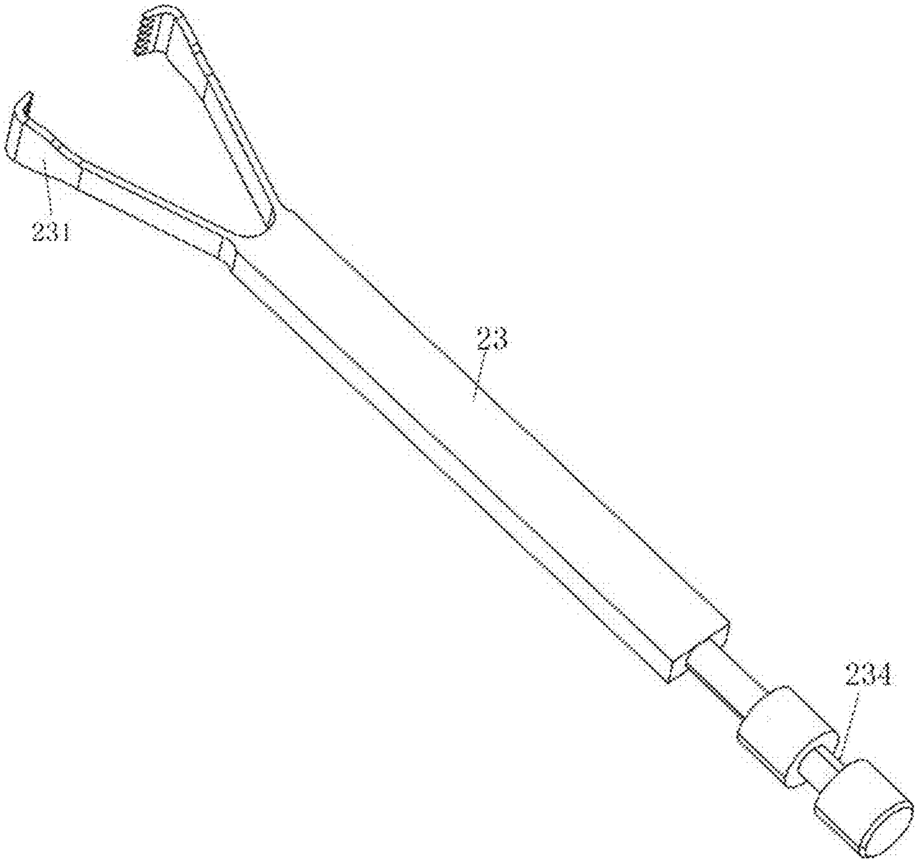
FIG. 27 is a structural schematic diagram II of the clamping rod of the present invention.
Figure 28:
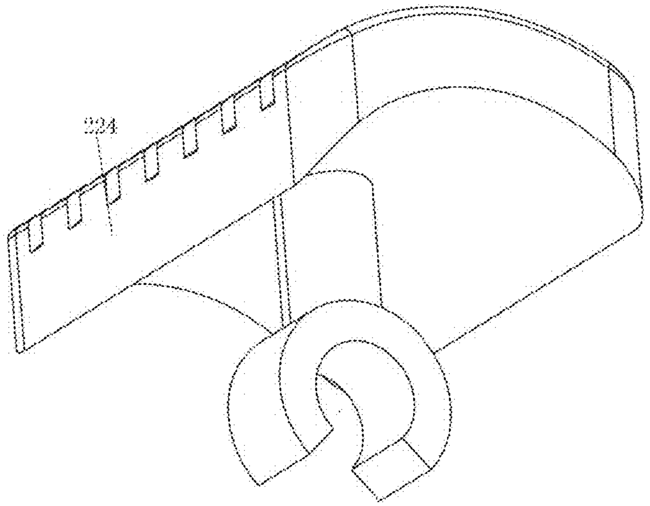
FIG. 28 is a structural schematic diagram I of a sleeve rod pushing member of the present invention.
Figure 29:
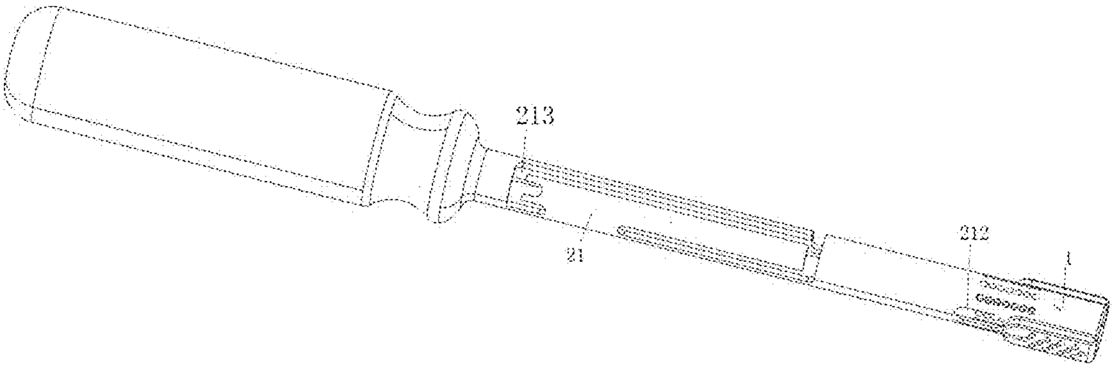
FIG. 29 is a structural schematic diagram of an outer tube of the present invention.
Figure 30:
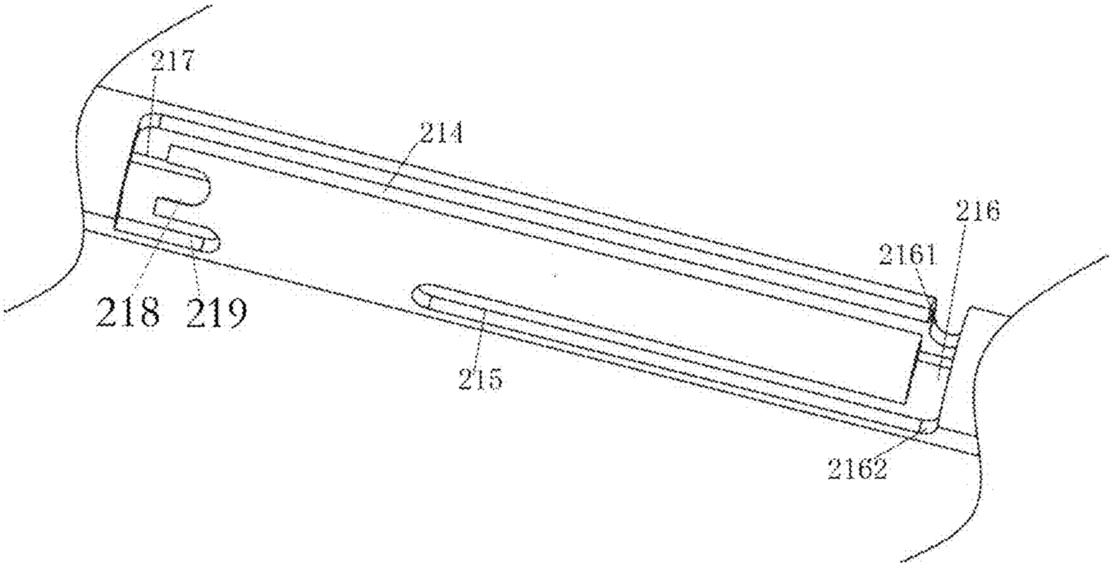
FIG. 30 is a local structural schematic diagram of the outer tube of the present invention.
Figure 31:
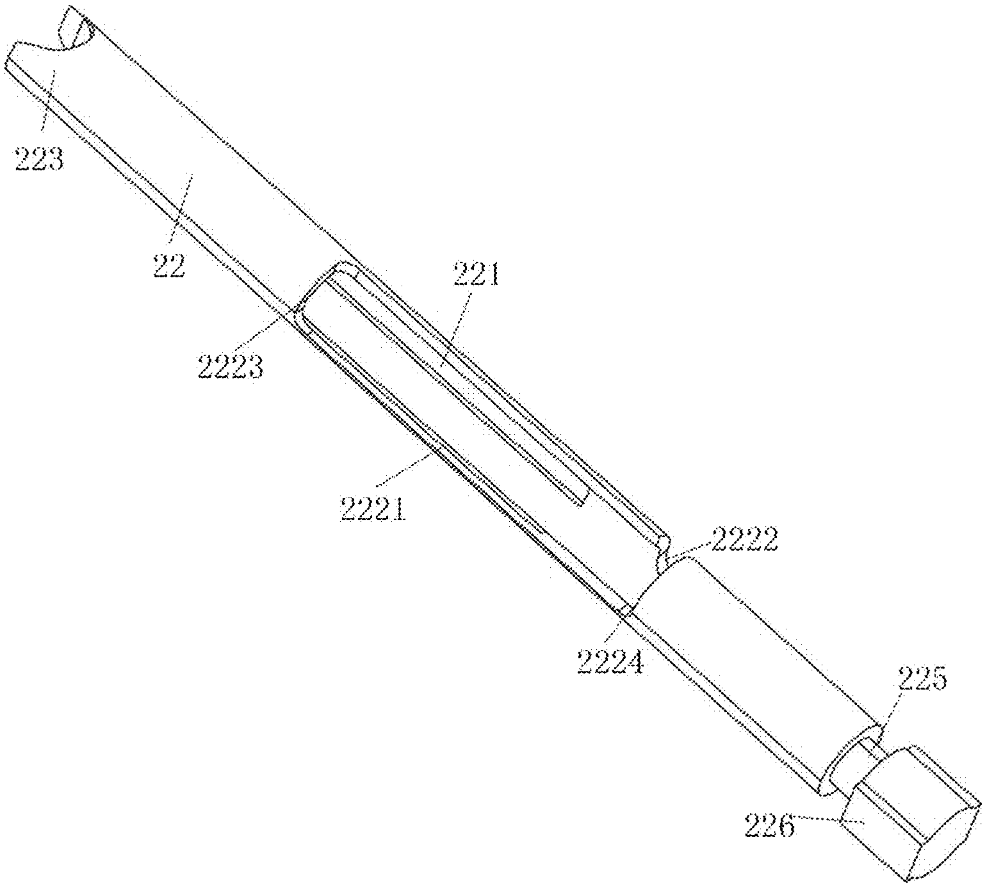
FIG. 31 is a structural schematic diagram I of a sleeve rod of the present invention.
Figure 32:
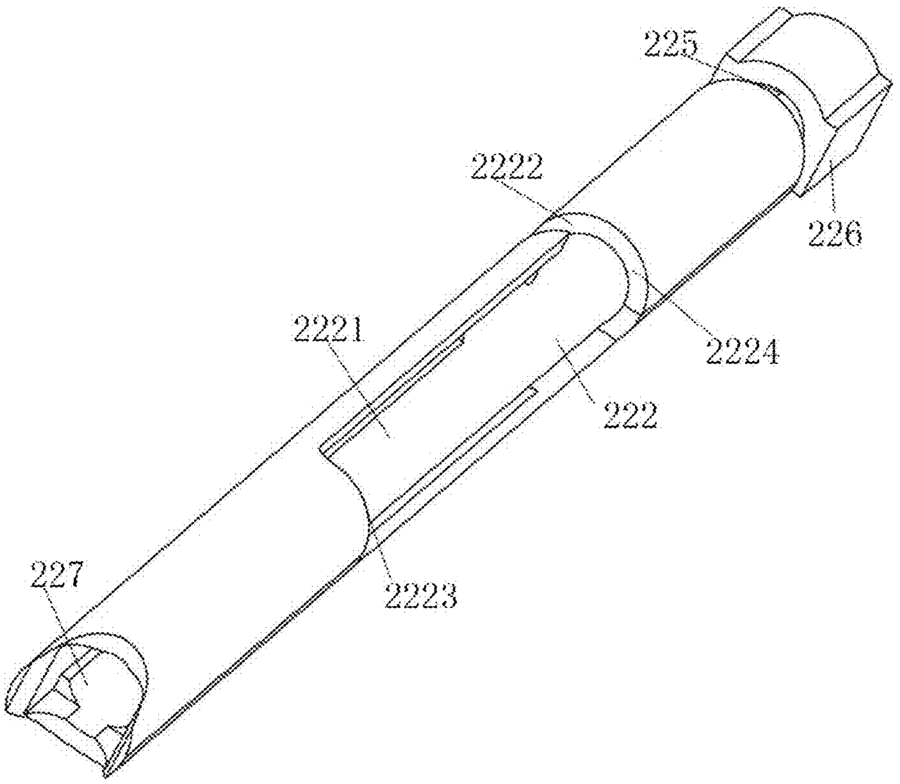
FIG. 32 is a structural schematic diagram II of the sleeve rod of the present invention.
Figure 33:
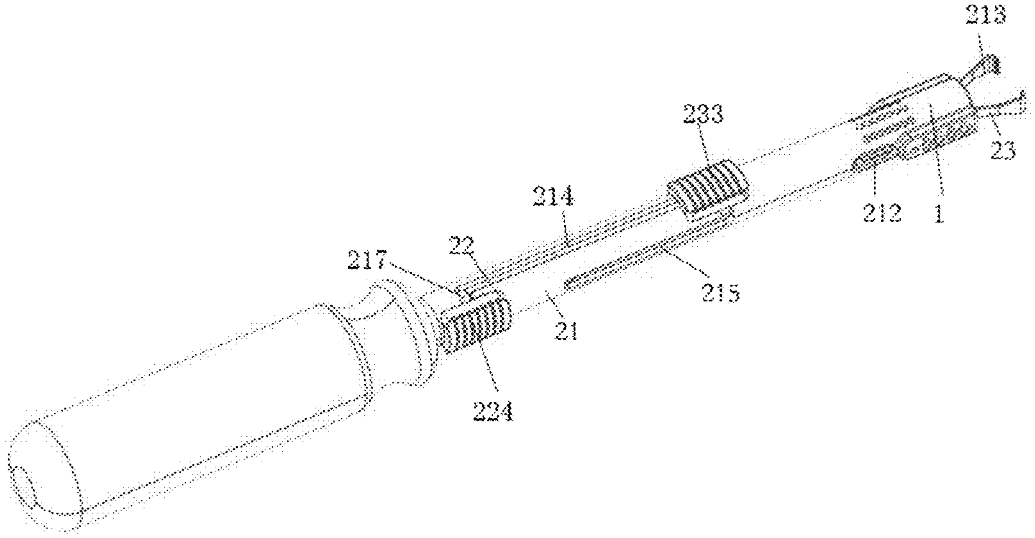
FIG. 33 is a schematic diagram I of steps for gripping and locking a tendon using a gripping element.

FIG. 22 is an effect diagram of suture by means of the guiding element of the improved Bunnel suture method, with a suture wire 103 presenting U-shaped threading. The needle guide holes 13 include a casting-on hole, a casting-off hole, and several intermediate holes. The casting-on hole, the casting-off hole, and the several intermediate holes are all perpendicular to the wiring channels 14, while the casting-on hole, the casting-off hole, and the several intermediate holes are all parallel to each other. In this embodiment, double-needle suture can be used, where one suture needle 101 starts casting-on from the casting-on hole a1 or b1 of the wall 12 of the chamber. At this time, two suture needles 101 are located near a left wall 121 and a right wall 122, respectively. When a1 is used as the casting-on hole, the order of needling is a1, a3, b3, b5, a5, a6, and b6 in sequence; when b1 is used as the casting-on hole, the order of needling is b1, b2, a2, a4, b4, b6, and a6 in sequence.

Gripping Element

As shown in FIGS. 25-33, a gripping element includes an outer tube 21 having an outer tube cavity 211, and a gripping component. The outer tube cavity 211 can be in communication with a chamber 10 of a guiding element. The outer tube 21 sleeves the gripping component. The gripping component is movable in the outer tube cavity 211 and the chamber 10. The gripping component can grip or release a tendon 100. The outer tube 21 and a guiding element 1 may be integrally formed or detachable connected. In the region where the outer tube 21 is connected to the guiding element 1, an observation window 212 that can observe the tendon 100 is arranged. Simply put, the main function of the gripping component is to grip the tendon 100 located outside the guiding element 1, then pull the tendon 100 into the chamber 10 of the guiding element 1, and fix the tendon 100 in the chamber 10. In this embodiment, the gripping function is achieved through the opening and closing of clamping claws, and the gripping component grips the end of a rupture opening of the tendon 100. Due to the ultimate goal of the surgery being to suture the two ends of the rupture opening of the tendon 100, the guiding element 1 guiding suture tools to suture the tendon 100 should also be near the end of the rupture opening of the tendon 100. Hence, gripping the end of the rupture opening of the tendon 100 by the gripping component to the chamber 10 of the guide element 1 can be stopped at the observation window 212. The observation window 212 is usually arranged near a functional region attachment of the guiding element 1. The gripping component should not pull too deep when gripping the rupture opening of the tendon 100 to the chamber 10, as too deep is not conducive to the docking of the two rupture openings.

The gripping component includes a clamping rod 23 having clamping claws 231, and a sleeve rod 22. The sleeve rod 22 sleeves the clamping rod 23. The relative movement of the sleeve rod 22 and the clamping rod 23 can cause the clamping claws 231 to open or close. The clamping rod 23 includes the clamping claws 231, a moving rod 232, a clamping rod pushing member 233, and a clamping rod annular groove 234. The moving rod 232 is usually a cuboid structure or is provided with a non-circular structure that can cooperate with the sleeve rod 22 to allow the moving rod 232 to only move back and forth along the sleeve rod 22 in one direction, and cannot allow the clamping rod 23 to rotate along the sleeve rod 22. In this embodiment, the moving rod 232 is a cuboid structure, and the sleeve rod 22 is provided with a sleeve rod guide groove 221 that can cooperate with the cuboid structure, thereby allowing the clamping rod 23 to move forward and backward along the sleeve rod 22 without rotation. One end of the moving rod 232 is provided with the clamping claws 231, and the other end thereof is provided with the clamping rod annular groove 234. The clamping rod pushing member 233 is arranged on the clamping rod annular groove 234 and can rotate along the clamping rod annular groove 234. In this embodiment, the clamping claws 231 include inward bending portions 2311, and the ends of the bending portions 2311 are provided with serrated grooves that can grip the tendon 100 more firmly.

The sleeve rod 22 is provided with an L-shaped sleeve rod groove 222. The sleeve rod groove 222 includes a first sleeve rod channel 2221 and a second sleeve rod channel 2222. The first sleeve rod channel 2221 is in vertical communication with the second sleeve rod channel 2222. The first sleeve rod channel 2221 is arranged in the direction of movement of the clamping rod 23. The clamping rod pushing member 233 can move along the sleeve rod groove 222. The first sleeve rod channel 2221 includes a first sleeve rod end 2223 and a second sleeve rod end 2224, and the second sleeve rod channel 2222 is in communication with the first sleeve rod end 2223. When the clamping rod pushing member 233 is moved to the first sleeve rod end 2223, a sleeve rod end opening 223 has already moved away from the clamping claws 231, and the clamping claws 231 are in an opened state. At this time, the clamping claws 231 can be used to grip the end of the rupture opening the tendon 100. After gripping is completed, the sleeve rod 22 is pushed. When the clamping rod pushing member 233 contacts the second sleeve rod end 2224, the clamping rod pushing member 233 is rotated to the second sleeve rod channel 2222. At this time, it can be considered that the clamping claws 231 are in a locked state. At this time, the sleeve rod end opening 223 is already located near the clamping claws 231 to lock the clamping claws 231, and the tendon 100 located in the clamping claws 231 can also be considered to be in a locked state.

The sleeve rod 22 further includes a sleeve rod pushing member 224, a sleeve rod annular groove 225, and a sleeve rod moving block 226. One end of the sleeve rod 22 is provided with a sleeve rod opening 227 that allows the clamping rod to pass out, and the other end thereof is provided with the sleeve rod moving block 226. The sleeve rod moving block 226 can cooperate with an outer tube guide groove 213 on the outer tube 21, so that the sleeve rod 22 can only move back and forth along the outer tube 21 in one direction, and cannot rotate along the outer tube 21.

When the clamping rod pushing member 233 is located at the first sleeve rod end 2223, the clamping claws 231 are in an opened state, the gripping component is in a release state, and the clamping rod 23 and the sleeve rod 22 are movable at this time. However, when the clamping rod pushing member 233 is located at the second sleeve rod end 2224, the clamping claws 231 are in a closed and unlocked state; when the clamping rod pushing member 233 is located in the second sleeve rod channel 2222, the clamping claws 231 are in a closed and locked state. At this time, the clamping claws 231 are in a closed state, and the clamping rod 23 and the sleeve rod 22 are also in a locked state at the same time, that is, at this time, the clamping rod 23 and the sleeve rod 22 can be moved simultaneously.

The outer tube 21 includes a first outer tube groove 214, a second outer tube groove 215, a third outer tube groove 216, and a fourth outer tube groove 217. The first outer tube groove 214, the second outer tube groove 215, the third outer tube groove 216, and the fourth outer tube groove 217 are in communication. The first outer tube groove 214 and the second outer tube groove 215 are parallel to each other and arranged in the direction of movement of the gripping component. The third outer tube groove 216 and the fourth outer tube groove 217 are parallel to each other, and both the third outer tube groove 216 and the fourth outer tube groove 217 are perpendicular to the first outer tube groove 214. The third outer tube groove 216 and the fourth outer tube groove 217 are arranged at two ends of the first outer tube groove 214, and the third outer tube groove 216 can be in communication with the first outer tube groove 214 and the second outer tube groove 215. The third outer tube groove 216 includes a first end 2161 and a second end 2162, the second outer tube groove 215 is arranged at the second end 2162, and one end of the first outer tube groove 214 is arranged between the first end 2161 and the second end 2162; the other end thereof is in communication with the fourth outer tube groove 217. The sleeve rod pushing member 224 can move on the first outer tube groove 214 and the fourth outer tube groove 217; the clamping rod pushing member 233 can move on the first outer tube groove 214, the second outer tube groove 215, and the third outer tube groove 216.

Figure 34:
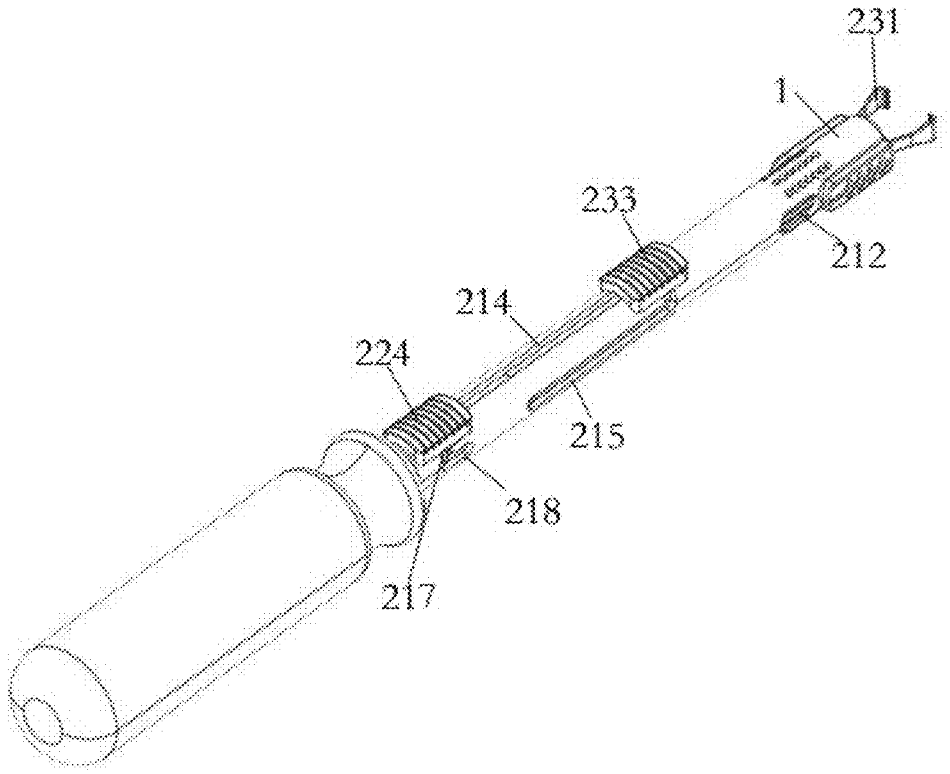
FIG. 34 is a schematic diagram II of the steps for gripping and locking the tendon using the gripping element.
Figure 35:
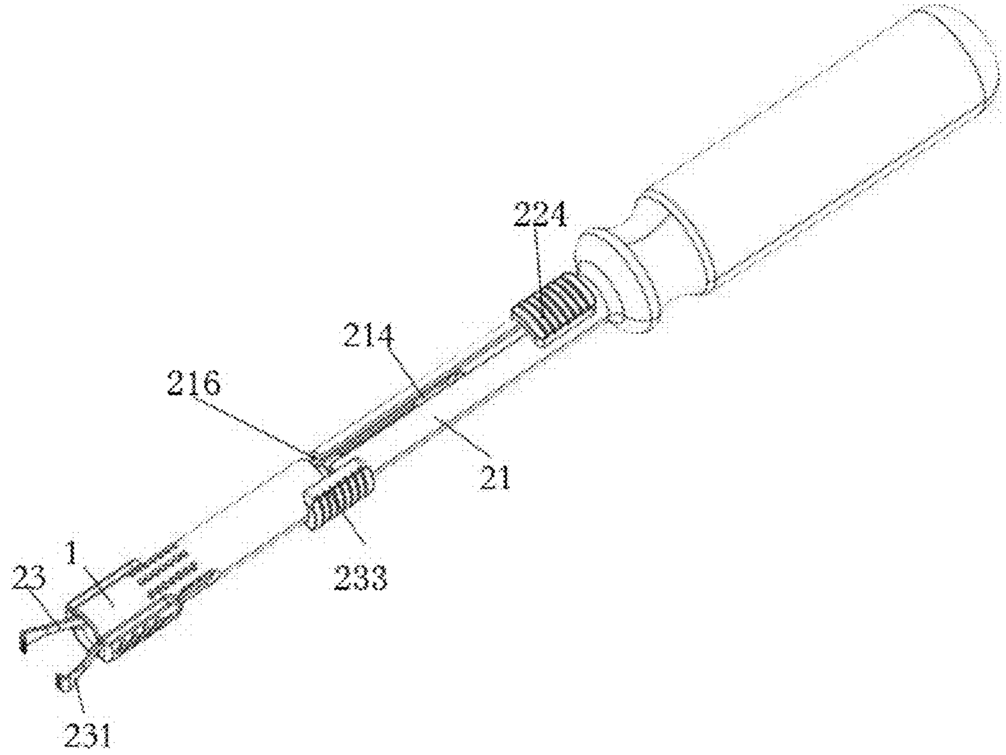
FIG. 35 is a schematic diagram III of the steps for gripping and locking the tendon using the gripping element.
Figure 36:
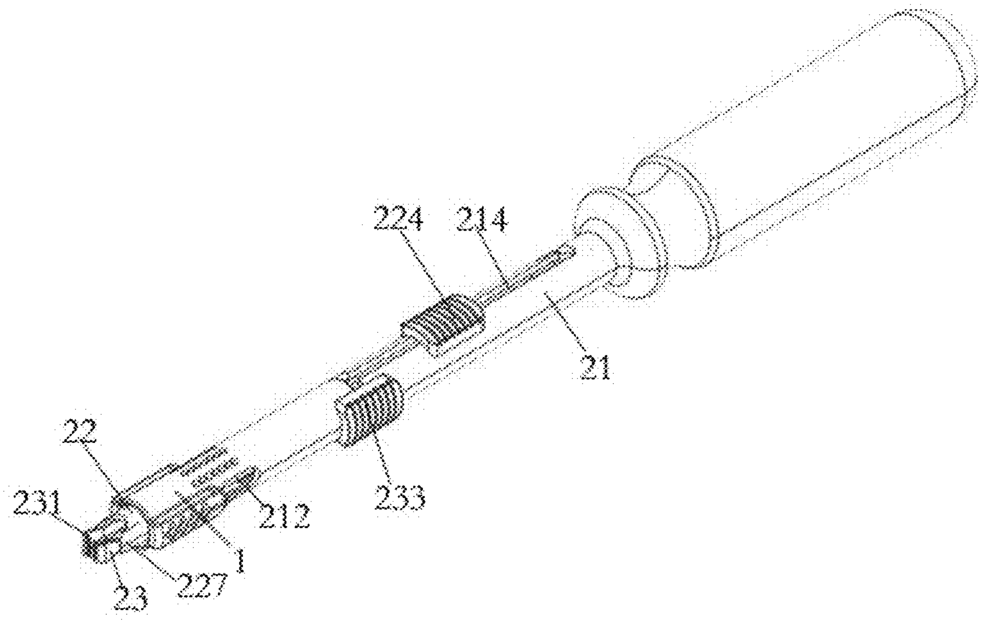
FIG. 36 is a schematic diagram IV of the steps for gripping and locking the tendon using the gripping element.
Figure 37:
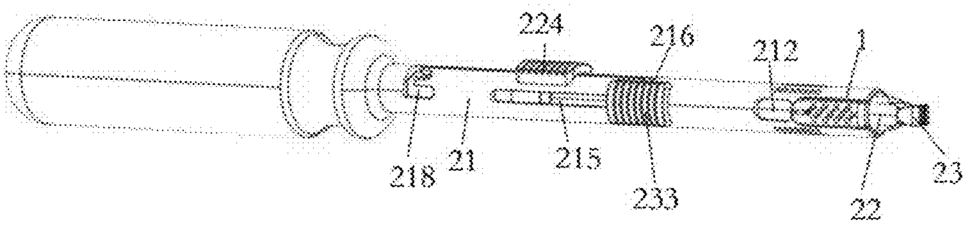
FIG. 37 is a schematic diagram V of the steps for gripping and locking the tendon using the gripping element.
Figure 38:
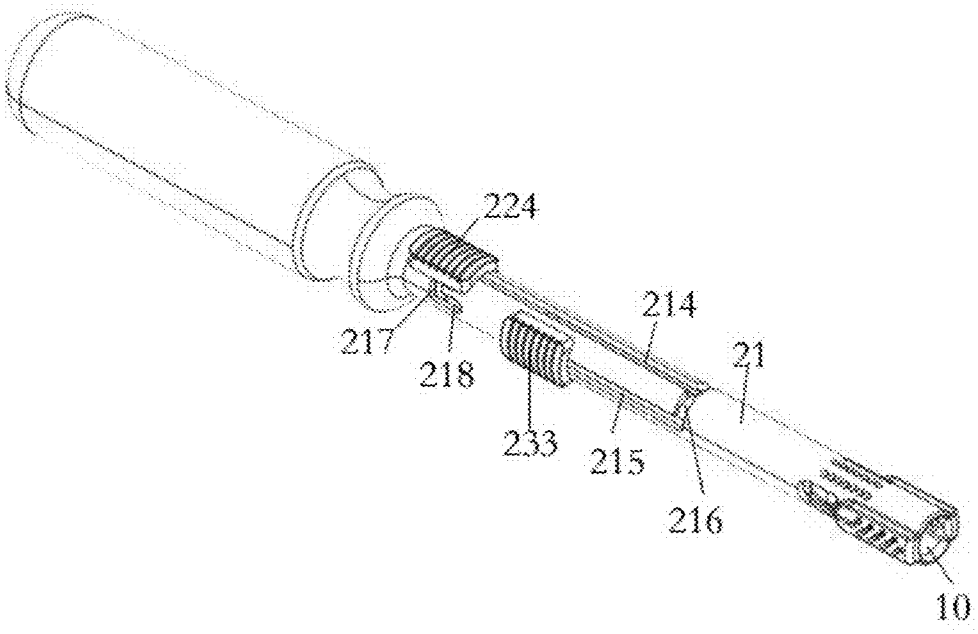
FIG. 38 is a schematic diagram VI of the steps for gripping and locking the tendon using the gripping element.
Figure 39:
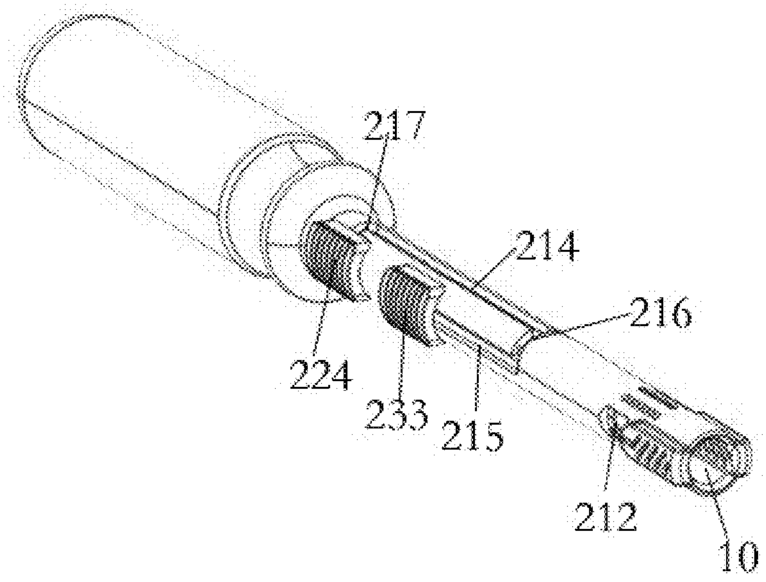
FIG. 39 is a schematic diagram VII of the steps for gripping and locking the tendon using the gripping element.
Figure 40:
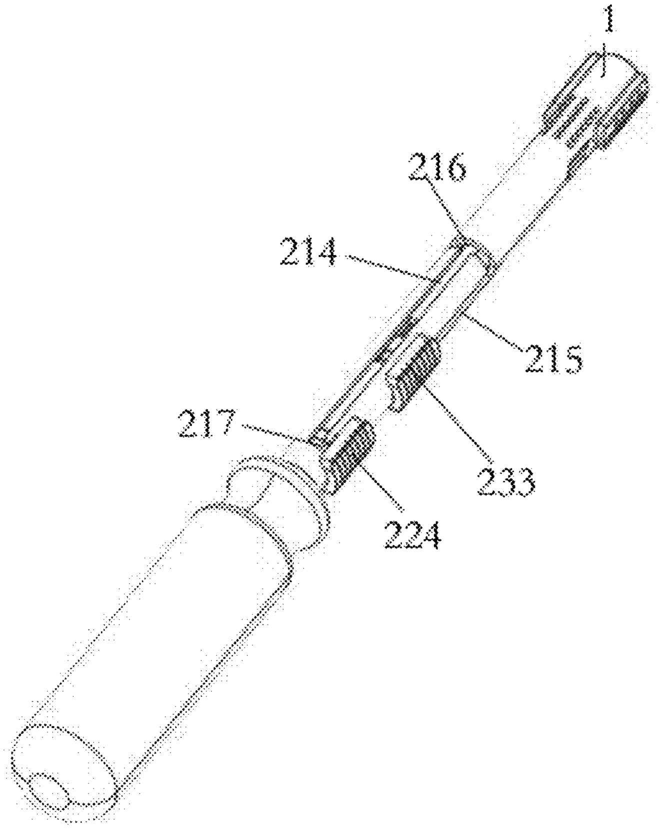
FIG. 40 is a schematic diagram VIII of the steps for gripping and locking the tendon using the gripping element.

As shown in FIGS. 33-40, the specific operation steps of the tendon suture instrument are as follows: in an initial state (FIG. 33), both the clamping rod 23 and the sleeve rod 22 are located in the outer tube 21, the clamping rod pushing member 233 is located on the first outer tube groove 214, and the sleeve rod pushing member 224 is located on the fourth outer tube groove 217. Step 1 (as shown in FIG. 34): firstly, the sleeve rod pushing member 224 is rotated to the connection position between the fourth outer tube groove 217 and the first outer tube groove 214, at this time, both the sleeve rod pushing member 224 and the clamping rod pushing member 233 are located on the first outer tube groove 214, the clamping rod pushing member 223 is pushed along the first outer tube groove 214 to the third outer tube groove 216, at this time, the clamping claws 231 of the clamping rod are pushed out of the guiding element 1, and the clamping claws 231 are in a release state; Step 2 (as shown in FIG. 35): the clamping rod pushing member 233 is rotated along the third outer tube groove 216 to the first end 2161 of the third outer tube groove 216, at this time, the clamping rod 23 and the outer tube 21 are in a fixed state, the clamping rod 23 cannot be moved, at this time, the clamping claws 231 can be used to clamp the end of the rupture opening of the tendon 100; Step 3 (as shown in FIG. 36), after the clamping claws 231 clamp the tendon 100, the sleeve rod pushing member 224 is pushed to the extreme position, at this time, the sleeve rod opening 227 begins to approach the clamping claws 231, the clamping claws 231 are locked by the sleeve rod 22, and at this time, it can be considered that the tendon 100 has been locked on the clamping claws 231; Step 4 (as shown in FIG. 37): the clamping rod pushing member 233 is rotated along the third outer tube groove 216 to the second end 2162, the clamping rod pushing member 233 is also located on the second outer tube groove 215, and at this time, the clamping rod 23 and the sleeve rod 22 are locked, that is, the clamping rod 23 and the sleeve rod 22 can be moved simultaneously; Step 5 (as shown in FIG. 38): the sleeve rod pushing member 224 is moved back along the first outer tube groove 214 to the junction of the first outer tube groove 214 and the fourth outer tube groove 217, at this time, the clamping rod pushing member 233 also moves along the second outer tube groove 215 at the same time, the sleeve rod pushing member 224 and the clamping rod pushing member 233 move simultaneously and the distance of movement is also the same, and at this time, the clamping claws 231 with the tendon 100 are moved into the chamber 10 of the guiding element 1; Step 6 (as shown in FIGS. 39 and 40): the sleeve rod pushing member 224 is rotated along the fourth outer tube groove 217 provided with a locking groove 218, and the sleeve rod pushing member 224 is pushed into the locking groove 218, so that the clamping rod 23 and the sleeve rod 22 can be fully locked; the tendon 100 clamped by the clamping claws 231 is also considered fully locked; at this point, the guiding element 1 can guide the suture tools to suture the tendon 100. Additionally, it needs to be noted that the locking groove 218 includes a first locking groove 218 and a second locking groove 219. The depth of the first locking groove 218 is less than that of the second locking groove 219. This design is to facilitate the adjusting of the position of the clamping claws 231 in the guiding element 1. That is, when the sleeve rod pushing member 224 is located in the first locking groove 218, the clamping claws 231 are farther away from the opening 11 of the chamber 10; when the sleeve rod pushing member 224 is located in the second locking groove 219, the clamping claws 231 are closer to the opening 11 of the chamber 10. The surgeon can make slight adjustments to the clamping claws 231 based on the actual suture situation. After the suture is completed, only the above steps need to be reversed to complete the release of the tendon 100 by the clamping claws 231, so they will not be repeated.

All embodiments as below are also belong to the Invention:

1. A tendon suture instrument, comprising a chamber for accommodating a tendon tissue, wherein one end of the chamber is provided with an opening, the opening is arranged to allow the tendon tissue to enter the chamber, the chamber is defined by a wall, and a first wiring channel and a first needle guide hole are arranged on the wall.
2. The tendon suture instrument according to clause 1, wherein the first wiring channel comprises the first needle guide hole, a side wall of the chamber comprises a second wiring channel comprising a third needle guide hole, and the first wiring channel and the second wiring channel are distributed on two sides of the chamber.
3. The tendon suture instrument according to clause 2, wherein the first needle guide hole of the first wiring channel is arranged to guide a suture needle to pass through a cross section of the chamber and then exit from the third needle guide hole of the second wiring channel.
4. The tendon suture instrument according to clause 3, wherein a second needle guide hole is arranged on the first wiring channel, and the first needle guide hole and the second needle guide hole are distributed at two ends of the first wiring channel; and the second wiring channel further comprises a fourth needle guide hole, and the third needle guide hole and the fourth needle guide hole are distributed at two ends of the second wiring channel.
5. The tendon suture instrument according to clause 4, wherein the first wiring channel and the second wiring channel are arranged axisymmetrically along the chamber; a third wiring channel is arranged near a same side as the first wiring channel, a fourth wiring channel is arranged near a same side as the second wiring channel, and a fifth needle guide hole and a sixth needle guide hole are arranged at two ends of the third wiring channel; and a seventh needle guide hole and an eighth needle guide hole are arranged at two ends of the fourth wiring channel.
6. The tendon suture instrument according to clause 5, wherein the first needle guide hole of the first wiring channel is arranged to guide a first suture needle to pass into and out of the third needle guide hole of the second wiring channel, and then the fourth needle guide hole of the second wiring channel is arranged again to guide the first suture needle to pass into and out of the sixth needle guide hole of the third wiring channel.
7. The tendon suture instrument according to clause 1, wherein the first wiring channel is arranged on a side wall of the chamber along a longitudinal direction of the chamber, and a second wiring channel is arranged symmetrical to the first wiring channel along a longitudinal axis of the chamber, alternatively, both the first wiring channel and the second wiring channel are arranged along the longitudinal direction of the chamber and distributed on two sides of the chamber.
8. The tendon suture instrument according to clause 7, wherein the first needle guide hole, a second needle guide hole and a third needle guide hole are arranged sequentially on the first wiring channel, and a fourth needle guide hole, a fifth needle guide hole and a sixth needle guide hole are arranged sequentially on the second wiring channel, wherein the first needle guide hole and the fourth needle guide hole are arranged in a symmetrical communication manner, the second needle guide hole and the sixth needle guide hole are arranged in a communication manner, and the third needle guide hole and the fifth needle guide hole are arranged in a communication manner.
9. The tendon suture instrument according to clause 8, wherein when a first suture needle and a second suture needle connected to a suture wire are used for tendon suture, the first suture needle can enter from the first needle guide hole of the first wiring channel and exit from the fourth needle guide hole of the second wiring channel, so that the first suture needle is located on one side of the second wiring channel, and the second suture needle is distributed on one side of the first wiring channel.
10. The tendon suture instrument according to clause 9, wherein the first suture needle can enter from the fifth needle guide hole and exit from the third needle guide hole, the second suture needle enters from the second needle guide hole and exits from the sixth needle guide hole, and the suture wire is arranged on a tendon in a cross manner if the tendon tissue is contained in the chamber.

11. The tendon suture instrument according to clause 1, wherein a second wiring channel is arranged on a same side as the first wiring channel on the wall of the chamber, and a third wiring channel and a fourth wiring channel are arranged symmetrical to the first wiring channel and the second wiring channel on the wall of the chamber, wherein the first wiring channel is not in communication with the second wiring channel, and the third wiring channel is not in communication with the fourth wiring channel.

12. The tendon suture instrument according to clause 11, wherein a length of the first wiring channel is less than that of the second wiring channel, alternatively, a length of the third wiring channel is greater than that of the fourth wiring channel.

13. The tendon suture instrument according to clause 12, wherein a projection of the first wiring channel is located in or on the third wiring channel, or the length of the first wiring channel is less than that of the third wiring channel; or a length of the fourth wiring channel is less than that of the second wiring channel.

14. The tendon suture instrument according to clause 13, wherein one or more needle guide holes are arranged on the first wiring channel, the second wiring channel, the third wiring channel, and the fourth wiring channel.

15. The tendon suture instrument according to clause 14, wherein the first wiring channel, the second wiring channel, the third wiring channel, and the fourth wiring channel are arranged along a longitudinal direction of the chamber.

16. The tendon suture instrument according to clause 1, wherein a second wiring channel is arranged on a same side as the first wiring channel on a side wall of the chamber, and one or more needle guide holes are arranged on each wiring channel.

17. The tendon suture instrument according to clause 16, wherein the first needle guide hole and a second needle guide hole are arranged at two ends of the first wiring channel, and a third needle guide hole and a fourth needle guide hole are arranged at two ends of the second wiring channel, so that when the needle guide holes are used to guide a suture needle to move, the suture needle enters from the needle guide hole at one end of the first wiring channel and exits from the needle guide hole of the second wiring channel.

18. The tendon suture instrument according to clause 16, wherein the first wiring channel is close to the second wiring channel, or the first wiring channel is arranged parallel to the second wiring channel, and the suture needle can pass between the first wiring channel and the second wiring channel.

19. The tendon suture instrument according to clause 16, wherein the first wiring channel and the second wiring channel are arranged on a same side on the wall of the chamber, the first needle guide hole and a second needle guide hole are arranged on the first wiring channel, and a third needle guide hole and a fourth needle guide hole are arranged on the second wiring channel; and when first suture is performed, a suture needle enters from the second needle guide hole of the first wiring channel and then exits from the third needle guide hole of the second wiring channel.

20. The tendon suture instrument according to clause 19, wherein the same side on the wall further comprises a third wiring channel, a fifth needle guide hole and a sixth needle guide hole are arranged on the third wiring channel, and when suture is performed again, the suture needle enters from the fourth needle guide hole of the second wiring channel and exits from the fifth needle guide hole of the third wiring channel, so that a suture wire is arranged on a surface of a tendon through the wiring channels if the tendon is located in the chamber.

21. A tendon suture instrument, comprising a chamber, wherein one end of the chamber is provided with an opening, the chamber is used for accommodating a sutured tendon tissue, the tendon tissue can enter the chamber through the opening of the chamber when needing to be sutured, the chamber is defined by a wall, and a wiring region is arranged on the wall, wherein one or more needle guide holes are arranged on the wiring region.

22. The tendon suture instrument according to clause 21, wherein the needle guide holes are arranged on two sides of the wiring region.

23. The tendon suture instrument according to clause 22, wherein the wiring region is all missing regions of a side wall of the chamber.

24. The tendon suture instrument according to clause 22, wherein the wiring region is located on one side of the chamber, one or two or more needle guide holes are arranged on one side of the wiring region along a longitudinal direction of the chamber, and one or two or more needle guide holes are correspondingly arranged on the other side or edge of the wiring region.

25. The tendon suture instrument according to clause 22, wherein when a suture needle is allowed to pass out of the needle guide hole on one side of the wiring region, a suture wire is allowed to surround a needle head one round, and then the needle head is allowed to pass through a region formed by the suture wire.

26. The tendon suture instrument according to clause 25, wherein the suture wire surrounds the needle head in a clockwise or counterclockwise direction.

27. The tendon suture instrument according to clause 22, wherein a third needle guide hole and a fifth needle guide hole are arranged on one side of the wiring region, the needle guide holes are arranged to allow a needle head of a suture needle to come out, a fourth needle guide hole and a sixth needle guide hole are arranged on an opposite side of the wiring region, and the needle guide holes are for the needle head to enter, so that when suture is performed using the suture needle, the suture needle is allowed to come out of the third needle guide hole, when a needle tip comes out, a suture wire passes clockwise in front of the needle tip, and then the suture needle is allowed to pass through a region surrounded by the suture wire, thus forming a knot at the third needle guide hole.

28. The tendon suture instrument according to clause 27, wherein when the suture needle enters again from the fourth needle guide hole and exits from the fifth needle guide hole, when the needle tip comes out, the suture wire passes clockwise in front of the needle tip, and then the suture needle is allowed to pass through a region surrounded by the suture wire, thus forming a knot at the fifth needle guide hole.

29. The tendon suture instrument according to clause 28, wherein the third and fourth needle guide holes and the fifth and sixth needle guide holes are distributed on the two sides of the wiring region, and the third needle guide hole and the fourth needle guide hole are not in a same straight line, or the fifth needle guide hole and the sixth needle guide hole are likewise not in a same straight line; alternatively, a connecting line of the third needle guide hole and the fifth needle guide hole is parallel to a connecting line of the fourth needle guide hole and the sixth needle guide hole.

30. The tendon suture instrument according to one of clauses 1-29, further comprising a gripping element that is arranged to enable the tendon to pass through an inlet of the chamber and be located in the chamber, thereby fixing the tendon in the chamber or allowing the tendon to be released from the chamber.

31. The tendon suture instrument according to clause 30, wherein the grabbing element has an opened or closed state, or preferably, such opening or closing is automatically formed.

32. The tendon suture instrument according to clause 31, further comprising an outer tube having a cavity, wherein the gripping element is located in the cavity of the outer tube, and relative motion between the gripping element and the outer tube controls the opened or closed state of the gripping element.

33. The tendon suture instrument according to clause 32, wherein the gripping element and the outer tube are movable in the chamber, so that by means of movement, the tendon is allowed to be gripped by the gripping element and thus enter the chamber through an opening, alternatively, the gripping element is allowed to be opened to release the tendon from the chamber so as to detach from the chamber.

All patents and publications mentioned in the specification of the present invention indicate that they are publicly available technologies in the art and can be used in the present invention. All patents and publications cited here are likewise listed in the references, just like each publication being specifically referenced and cited separately. The present invention described here can be implemented in the absence of any one or more elements and one or more limitations that are not specifically stated here. For example, in each embodiment here, the terms “including”, “substantially consisting of”, and “consisting of” can be replaced with the remaining two terms of either. The “one” here only means “one”, and it is not ruled out that it includes only one, and can also mean including two or more. The terms and expressions used here are descriptive and not limited by them, and there is no any intention here to indicate that these terms and explanations described in herein exclude any equivalent features. However, it can be known that any appropriate changes or amendments may be made within the scope of the present invention and claims. It can be understood that the embodiments described in the present invention are all preferred embodiments and features, and any general skilled person in the art can make some modifications and variations based on the essence of description of the present invention. These modifications and variations are also considered to fall within the scope of the present invention and the scope limited by independent claims and dependent claims.

The invention claimed is:

1. A tendon suture instrument, comprising a chamber for accommodating a tendon tissue, wherein one end of the chamber is provided with an opening, the opening is arranged to allow the tendon tissue to enter the chamber, the chamber is defined by a side wall, and a first wiring channel and a first needle guide hole are arranged on the side wall; wherein the tendon suture instrument further comprises a gripping element configured to grip and pull the tendon tissue into the chamber through the opening, thereby fixing the tendon tissue in the chamber or allowing the tendon tissue to leave the chamber wherein the chamber is formed at a distal end of the gripping element.

2. The tendon suture instrument according to claim 1, wherein the first wiring channel comprises the first needle guide hole, the side wall of the chamber comprises a second wiring channel comprising a third needle guide hole, and the first wiring channel and the second wiring channel are distributed on two sides of the chamber.

3. The tendon suture instrument according to claim 2, wherein the first needle guide hole of the first wiring channel is arranged to guide a first suture needle to pass through a cross section of the chamber and then exit from the third needle guide hole of the second wiring channel.

4. The tendon suture instrument according to claim 3, wherein a second needle guide hole is arranged on the first wiring channel, and the first needle guide hole and the second needle guide hole are distributed at two ends of the first wiring channel; and the second wiring channel further comprises a fourth needle guide hole, and the third needle guide hole and the fourth needle guide hole are distributed at two ends of the second wiring channel.

5. The tendon suture instrument according to claim 4, wherein the first wiring channel and the second wiring channel are arranged axisymmetrically along the chamber; a third wiring channel is arranged near a same side as the first wiring channel, a fourth wiring channel is arranged near a same side as the second wiring channel, and a fifth needle guide hole and a sixth needle guide hole are arranged at two ends of the third wiring channel; and a seventh needle guide hole and an eighth needle guide hole are arranged at two ends of the fourth wiring channel.

6. The tendon suture instrument according to claim 5, wherein the first needle guide hole of the first wiring channel is arranged to guide the first suture needle to pass into and out of the third needle guide hole of the second wiring channel, and then the fourth needle guide hole of the second wiring channel is arranged again to guide the first suture needle to pass into and out of the sixth needle guide hole of the third wiring channel.

7. The tendon suture instrument according to claim 1, wherein the first wiring channel is arranged on the side wall of the chamber along a longitudinal direction of the chamber, and a second wiring channel is arranged symmetrical to the first wiring channel along a longitudinal axis of the chamber, alternatively, both the first wiring channel and the second wiring channel are arranged along the longitudinal direction of the chamber and distributed on two sides of the chamber.

8. The tendon suture instrument according to claim 7, wherein the first needle guide hole, a second needle guide hole and a third needle guide hole are arranged sequentially on the first wiring channel, and a fourth needle guide hole, a fifth needle guide hole and a sixth needle guide hole are arranged sequentially on the second wiring channel, wherein the first needle guide hole and the fourth needle guide hole are arranged in a symmetrical communication manner, the second needle guide hole and the sixth needle guide hole are arranged in a communication manner, and the third needle guide hole and the fifth needle guide hole are arranged in a communication manner.

9. The tendon suture instrument according to claim 8, wherein when a first suture needle and a second suture needle connected to a suture wire are used for tendon suture, the first suture needle can enter from the first needle guide hole of the first wiring channel and exit from the fourth needle guide hole of the second wiring channel, so that the first suture needle is located on one side of the second wiring channel, and the second suture needle is distributed on one side of the first wiring channel.

10. The tendon suture instrument according to claim 9, wherein the first suture needle can enter from the fifth needle guide hole and exit from the third needle guide hole, the second suture needle enters from the second needle guide hole and exits from the sixth needle guide hole, and the suture wire is arranged on a tendon in a cross manner if the tendon tissue is contained in the chamber.

11. The tendon suture instrument according to claim 1, wherein a second wiring channel is arranged on a same side as the first wiring channel on the side wall of the chamber, and a third wiring channel and a fourth wiring channel are arranged symmetrical to the first wiring channel and the second wiring channel on the side wall of the chamber, wherein the first wiring channel is not in communication with the second wiring channel, and the third wiring channel is not in communication with the fourth wiring channel.

12. The tendon suture instrument according to claim 11, wherein a length of the first wiring channel is less than that of the second wiring channel, alternatively, a length of the third wiring channel is greater than that of the fourth wiring channel.

13. The tendon suture instrument according to claim 12, wherein a projection of the first wiring channel is located in or on the third wiring channel, or the length of the first wiring channel is less than that of the third wiring channel; or a length of the fourth wiring channel is less than that of the second wiring channel.

14. The tendon suture instrument according to claim 13, wherein one or more needle guide holes are arranged on the first wiring channel, the second wiring channel, the third wiring channel, and the fourth wiring channel.

15. The tendon suture instrument according to claim 14, wherein the first wiring channel, the second wiring channel, the third wiring channel, and the fourth wiring channel are arranged along a longitudinal direction of the chamber.

16. The tendon suture instrument according to claim 1, wherein a second wiring channel is arranged on a same side as the first wiring channel on the side wall of the chamber, and at least one other needle guide hole is arranged on each wiring channel.

17. The tendon suture instrument according to claim 16, wherein the first needle guide hole and a second needle guide hole are arranged at two ends of the first wiring channel, and a third needle guide hole and a fourth needle guide hole are arranged at two ends of the second wiring channel, so that when the first, second, third, fourth needle guide holes are used to guide a suture needle to move, the suture needle enters from the first or second needle guide hole at one end of the first wiring channel and exits from the third or fourth needle guide hole of the second wiring channel.

18. The tendon suture instrument according to claim 17, wherein the first wiring channel is close to the second wiring channel, or the first wiring channel is arranged parallel to the second wiring channel, and the suture needle can pass between the first wiring channel and the second wiring channel.

19. The tendon suture instrument according to claim 16, wherein the first wiring channel and the second wiring channel are arranged on a same side on the side wall of the chamber, the first needle guide hole and a second needle guide hole are arranged on the first wiring channel, and a third needle guide hole and a fourth needle guide hole are arranged on the second wiring channel; and when first suture is performed, a suture needle enters from the second needle guide hole of the first wiring channel and then exits from the third needle guide hole of the second wiring channel.

20. A tendon suture instrument, comprising a chamber, wherein one end of the chamber is provided with an opening, the chamber is used for accommodating a sutured tendon tissue, the tendon tissue can enter the chamber through the opening of the chamber when needing to be sutured, the chamber is defined by a side wall, and a wiring region is arranged on the side wall, wherein one or more needle guide holes are arranged on the wiring region; wherein the tendon suture instrument further comprises a gripping element configured to grip and pull the tendon tissue into the chamber through the opening, thereby fixing the tendon tissue in the chamber or allowing the tendon tissue to leave the chamber wherein the chamber is formed at a distal end of the gripping element" after "leave the chamber.

* * * * *